US011571397B2

(12) United States Patent
Martin

(10) Patent No.: US 11,571,397 B2
(45) Date of Patent: Feb. 7, 2023

(54) COMPOSITIONS AND METHODS FOR TREATING SEIZURE-INDUCED SUDDEN DEATH

(71) Applicant: ZOGENIX INTERNATIONAL LIMITED, Berkshire (GB)

(72) Inventor: Parthena Martin, Emeryville, CA (US)

(73) Assignee: ZOGENIX INTERNATIONAL LIMITED, Berkshire (GB)

( * ) Notice: Subject to any disclaimer, the term of this patent is extended or adjusted under 35 U.S.C. 154(b) by 644 days.

(21) Appl. No.: 16/340,009

(22) PCT Filed: May 11, 2018

(86) PCT No.: PCT/US2018/032406
§ 371 (c)(1),
(2) Date: Apr. 5, 2019

(87) PCT Pub. No.: WO2019/216919
PCT Pub. Date: Nov. 14, 2019

(65) Prior Publication Data
US 2021/0330610 A1    Oct. 28, 2021

(51) Int. Cl.
*A61K 31/137* (2006.01)
*A61P 25/08* (2006.01)
*A61K 31/166* (2006.01)
*A61K 31/18* (2006.01)
*A61K 31/19* (2006.01)
*A61K 31/36* (2006.01)
*A61K 31/404* (2006.01)
*A61K 31/439* (2006.01)
*A61K 31/445* (2006.01)
*A61K 31/4468* (2006.01)
*A61K 31/46* (2006.01)
*A61K 31/5375* (2006.01)
*A61K 31/5513* (2006.01)

(52) U.S. Cl.
CPC .......... *A61K 31/137* (2013.01); *A61K 31/166* (2013.01); *A61K 31/18* (2013.01); *A61K 31/19* (2013.01); *A61K 31/36* (2013.01); *A61K 31/404* (2013.01); *A61K 31/439* (2013.01); *A61K 31/445* (2013.01); *A61K 31/4468* (2013.01); *A61K 31/46* (2013.01); *A61K 31/5375* (2013.01); *A61K 31/5513* (2013.01); *A61P 25/08* (2018.01)

(58) Field of Classification Search
None
See application file for complete search history.

(56) References Cited

U.S. PATENT DOCUMENTS

| 3,117,160 A | 1/1964 | Holland |
|---|---|---|
| 3,198,833 A | 8/1965 | Beregi |
| 3,198,834 A | 8/1965 | Beregi et al. |
| 3,759,979 A | 9/1973 | Beregi et al. |
| 4,309,445 A | 1/1982 | Wurtman |
| 4,452,815 A | 6/1984 | Wurtman |
| 4,824,987 A | 4/1989 | Kleeman |
| 4,857,553 A | 8/1989 | Ward et al. |
| 5,587,398 A | 12/1996 | Elmaleh et al. |
| 5,808,156 A | 9/1998 | Cannata et al. |
| 5,811,586 A | 9/1998 | Cannata et al. |
| 5,834,477 A | 11/1998 | Mioduszewski |
| 5,985,880 A | 11/1999 | Chang |
| 6,045,501 A | 4/2000 | Elsayed et al. |
| 6,315,720 B1 | 11/2001 | Williams et al. |
| 6,561,976 B2 | 5/2003 | Elsayed et al. |
| 6,561,977 B2 | 5/2003 | Williams et al. |
| 6,599,901 B1 | 7/2003 | Flohr |
| 6,755,784 B2 | 6/2004 | Williams et al. |
| 6,869,399 B2 | 3/2005 | Williams et al. |
| 6,908,432 B2 | 6/2005 | Elsayed et al. |
| 7,141,018 B2 | 11/2006 | Williams et al. |
| 7,585,493 B2 | 9/2009 | Hale |
| 7,668,730 B2 | 2/2010 | Reardan et al. |
| 7,765,106 B2 | 7/2010 | Reardan et al. |
| 7,765,107 B2 | 7/2010 | Reardan et al. |

(Continued)

FOREIGN PATENT DOCUMENTS

| CN | 1425167 | 6/2003 |
|---|---|---|
| CN | 103025301 | 4/2013 |

(Continued)

OTHER PUBLICATIONS

Rémi et al., "Clinical features of the postictal state: Correlation with seizure variables", 2010, Epilepsy & Behavior, 19(2), pp. 114-117. (doi:10.1016/j.yebeh.2010.06.039)(Year: 2010).*

Thurman et al., "Sudden unexpected death in epilepsy: Assessing the public health burden", 2014, Epilepsia, 55(10):1479-1485. (doi: 10.1111/epi.12666) (Year: 2014).*

Subota et al., "Signs and symptoms of the postictal period in epilepsy: A systematic review and meta-analysis", 2019, Epilepsy & Behavior, 94, pp. 243-251. (doi.org/10.1016/j.yebeh.2019.03.014) (Year: 2019).*

(Continued)

*Primary Examiner* — My-Chau T. Tran
(74) *Attorney, Agent, or Firm* — Karl Bozicevic; Bozicevic, Field & Francis LLP

(57) ABSTRACT

5-HT receptor agonists are useful in the treatment of a variety of diseases. Provided herein are methods of reducing the incidence and/or severity of seizures in a human patient using a 5-HT receptor agonist, such as, for example, a 5-HT4 agonist (e.g., fenfluramine). Methods of treating epilepsy or epileptic encephalopathy, and/or reducing, ameliorating or eliminating incidence of SUDEP in a subject diagnosed with epilepsy by administering a 5-HT4 agonist (e.g., fenfluramine) to a subject in need thereof are provided. Pharmaceutical compositions for use in practicing the subject methods are also provided.

21 Claims, 14 Drawing Sheets

(56) References Cited

U.S. PATENT DOCUMENTS

| | | |
|---|---|---|
| 7,797,171 B2 | 9/2010 | Reardan et al. |
| 7,874,984 B2 | 1/2011 | Elsayed et al. |
| 7,895,059 B2 | 2/2011 | Reardan et al. |
| 7,959,566 B2 | 6/2011 | Williams et al. |
| 8,204,763 B2 | 6/2012 | Elsayed et al. |
| 8,263,650 B2 | 9/2012 | Cook et al. |
| 8,315,886 B2 | 11/2012 | Williams et al. |
| 8,386,274 B1 | 2/2013 | Pinsonneault |
| 8,457,988 B1 | 6/2013 | Reardan et al. |
| 8,589,182 B1 | 11/2013 | Reardan et al. |
| 8,589,188 B2 | 11/2013 | Elsayed et al. |
| 8,626,531 B2 | 1/2014 | Williams et al. |
| 8,731,963 B1 | 5/2014 | Reardan et al. |
| 9,125,900 B2 | 9/2015 | Meyer |
| 9,549,909 B2 * | 1/2017 | Ceulemens ............ A61P 43/00 |
| 9,603,814 B2 | 3/2017 | Ceulemens |
| 9,603,815 B2 | 3/2017 | Ceulemens |
| 9,610,260 B2 | 4/2017 | Ceulemens |
| 10,351,509 B2 | 7/2019 | Londesbrough |
| 10,351,510 B2 | 7/2019 | Londesbrough |
| 10,452,815 B2 | 10/2019 | Stewart et al. |
| 10,478,441 B2 | 11/2019 | Ceulemens |
| 10,478,442 B2 | 11/2019 | Ceulemens |
| 10,517,841 B1 | 12/2019 | Galer et al. |
| 10,603,290 B2 | 3/2020 | Farr |
| 10,682,317 B2 | 6/2020 | Abu-Izza |
| 10,689,324 B2 | 6/2020 | Farr |
| 10,947,183 B2 | 3/2021 | Londesbrough et al. |
| 10,950,331 B2 | 3/2021 | Stewart et al. |
| 10,952,976 B2 | 3/2021 | Galer |
| 11,040,018 B2 | 6/2021 | Farr |
| 11,352,882 B2 | 5/2022 | Farr |
| 2002/0038310 A1 | 3/2002 | Reitberg |
| 2002/0098175 A1 | 7/2002 | Zohoungbogbo |
| 2003/0007934 A1 | 1/2003 | Rabinowitz et al. |
| 2003/0118654 A1 | 6/2003 | Santos et al. |
| 2004/0249212 A1 | 12/2004 | Smallridge et al. |
| 2005/0182103 A1 | 8/2005 | Finke et al. |
| 2006/0121066 A1 | 6/2006 | Jaeger et al. |
| 2006/0270611 A1 | 11/2006 | Dries et al. |
| 2008/0004904 A1 | 1/2008 | Tran |
| 2008/0103179 A1 * | 5/2008 | Tam ................ A61P 3/10 514/326 |
| 2008/0243584 A1 | 10/2008 | Srinivasan |
| 2008/0261962 A1 | 10/2008 | Greer |
| 2009/0171697 A1 | 7/2009 | Glauser |
| 2010/0088778 A1 | 4/2010 | Mulley |
| 2010/0298181 A1 | 11/2010 | Hanada et al. |
| 2011/0092535 A1 | 4/2011 | Barnes et al. |
| 2011/0212171 A1 | 9/2011 | Venkatesh et al. |
| 2011/0230473 A1 | 9/2011 | Gordon et al. |
| 2012/0065999 A1 | 3/2012 | Takatoku |
| 2012/0107396 A1 | 5/2012 | Khan |
| 2012/0115958 A1 | 5/2012 | Mariotti et al. |
| 2012/0157392 A1 | 6/2012 | Martin et al. |
| 2012/0270848 A1 | 10/2012 | Mannion |
| 2012/0303388 A1 | 11/2012 | Vishnubhatla |
| 2013/0218586 A1 | 8/2013 | Huser |
| 2013/0296398 A1 | 11/2013 | Whalley |
| 2014/0030343 A1 | 1/2014 | Lamson |
| 2014/0142140 A1 | 5/2014 | Bird |
| 2014/0162942 A1 | 6/2014 | Ghosal |
| 2014/0329908 A1 | 11/2014 | Ceulemens et al. |
| 2014/0343044 A1 | 11/2014 | Ceulemens et al. |
| 2014/0343162 A1 | 11/2014 | Ceulemens et al. |
| 2014/0348966 A1 | 11/2014 | Balemba |
| 2015/0080377 A1 | 3/2015 | Dhanoa |
| 2015/0291597 A1 | 10/2015 | Mannion |
| 2015/0310187 A1 | 10/2015 | Rabinowitz |
| 2015/0359755 A1 | 12/2015 | Guy et al. |
| 2016/0136114 A1 | 5/2016 | Ceulemens et al. |
| 2016/0228454 A1 | 8/2016 | Zhang et al. |
| 2016/0249863 A1 | 9/2016 | Ando |
| 2016/0279159 A1 | 9/2016 | Hirano et al. |
| 2017/0020885 A1 | 1/2017 | Hsu |
| 2017/0056344 A1 | 3/2017 | Farr et al. |
| 2017/0071940 A1 | 3/2017 | Olaleye et al. |
| 2017/0071949 A1 | 3/2017 | De Witte et al. |
| 2017/0151194 A1 | 6/2017 | Ceulemens |
| 2017/0151214 A1 | 6/2017 | Ceulemens et al. |
| 2017/0151257 A1 | 6/2017 | Ceulemens |
| 2017/0151259 A1 | 6/2017 | Ceulemens |
| 2017/0174613 A1 | 6/2017 | Londesbrough et al. |
| 2017/0174614 A1 | 6/2017 | Farr et al. |
| 2017/0348303 A1 | 12/2017 | Bosse |
| 2018/0028499 A1 | 2/2018 | Baraban et al. |
| 2018/0055789 A1 | 3/2018 | Farr |
| 2018/0092864 A1 | 4/2018 | Martin et al. |
| 2018/0141953 A1 | 5/2018 | Dax |
| 2018/0148403 A1 | 5/2018 | Londesbrough et al. |
| 2018/0215701 A1 | 8/2018 | Carroll et al. |
| 2018/0325909 A1 | 11/2018 | DeWitte |
| 2019/0083425 A1 | 3/2019 | Farr |
| 2019/0091173 A1 | 3/2019 | Farfel |
| 2019/0091174 A1 | 3/2019 | Galer |
| 2019/0091175 A1 | 3/2019 | Morrison |
| 2019/0091176 A1 | 3/2019 | Galer |
| 2019/0091177 A1 | 3/2019 | Galer |
| 2019/0091179 A1 | 3/2019 | Morrison |
| 2019/0125697 A1 | 5/2019 | Farfel |
| 2019/0247333 A1 | 8/2019 | Farfel |
| 2019/0380979 A1 | 12/2019 | Galer |
| 2020/0030341 A1 | 1/2020 | Ceulemens |
| 2020/0170965 A1 | 6/2020 | Boyd |
| 2020/0261380 A1 | 8/2020 | Abu-Izza |
| 2020/0276136 A1 | 9/2020 | Galer |
| 2020/0297665 A1 | 9/2020 | Martin |
| 2020/0306210 A1 | 10/2020 | Morrison |
| 2020/0330406 A1 | 10/2020 | Galer |
| 2021/0113495 A1 | 4/2021 | Boyd |
| 2021/0121479 A1 | 4/2021 | Ceulemens |
| 2021/0147335 A1 | 5/2021 | Londesbrough |
| 2021/0158920 A1 | 5/2021 | Stewart et al. |
| 2021/0267916 A1 | 9/2021 | Farr |
| 2021/0299064 A1 | 9/2021 | Morrison |
| 2021/0393550 A1 | 12/2021 | Farr |
| 2021/0401776 A1 | 12/2021 | Martin |
| 2022/0008389 A1 | 1/2022 | Galer |
| 2022/0016053 A1 | 1/2022 | Galer |
| 2022/0096514 A1 | 3/2022 | Quan |
| 2022/0125743 A1 | 4/2022 | Farr |
| 2022/0133652 A1 | 5/2022 | Millet |
| 2022/0160727 A1 | 5/2022 | Ceulemens |

FOREIGN PATENT DOCUMENTS

| | | |
|---|---|---|
| CN | 103886415 | 6/2014 |
| DE | 2150399 | 4/1973 |
| EP | 0 441 160 | 8/1991 |
| EP | 0 920 864 | 6/1999 |
| EP | 1 399 015 | 1/2010 |
| EP | 2 399 513 | 12/2011 |
| EP | 3170807 | 5/2017 |
| GB | 1399015 | 6/1975 |
| GB | 2531282 | 4/2016 |
| HU | 204497 | 1/1992 |
| JP | A S64-066116 | 3/1989 |
| JP | H05-310564 A | 11/1993 |
| JP | A-2008-536545 | 9/2008 |
| JP | A-2009-525977 | 7/2009 |
| JP | A 2010-520162 | 6/2010 |
| JP | A-2011-221623 | 11/2011 |
| JP | A-2011-529923 | 12/2011 |
| JP | A-2012-511969 | 5/2012 |
| JP | A-2012-520130 | 9/2012 |
| JP | A-2012-208669 | 10/2012 |
| JP | A-2013-536857 | 9/2013 |
| JP | A-2013-248329 | 12/2013 |
| RU | 103209 | 3/2011 |
| RU | 2503448 | 1/2014 |
| RU | 2571501 | 12/2015 |
| WO | WO 1995/04713 | 2/1995 |
| WO | WO 1995/32962 | 12/1995 |
| WO | WO 2001/86506 | 11/2001 |

(56) References Cited

FOREIGN PATENT DOCUMENTS

| WO | WO 2003/026591 | 4/2003 |
|---|---|---|
| WO | WO 2003/077847 | 9/2003 |
| WO | WO 2005/004865 | 1/2005 |
| WO | WO 2006/100676 | 9/2006 |
| WO | WO 2007/073503 | 6/2007 |
| WO | WO 2007/092469 | 8/2007 |
| WO | WO 2008/025148 | 3/2008 |
| WO | WO 2008/104524 | 9/2008 |
| WO | WO 2009/087351 | 7/2009 |
| WO | WO 2010/015029 | 2/2010 |
| WO | WO 2010/020585 | 2/2010 |
| WO | WO 2010/025931 | 3/2010 |
| WO | WO 2010/075115 | 7/2010 |
| WO | WO 2010/104841 | 9/2010 |
| WO | WO 2010/121022 | 10/2010 |
| WO | WO 2011/112606 | 9/2011 |
| WO | WO 2011/146850 | 11/2011 |
| WO | WO 2012/030927 | 3/2012 |
| WO | WO 2013/096878 | 6/2013 |
| WO | WO 2013/122897 | 8/2013 |
| WO | WO 2014/177676 | 11/2014 |
| WO | WO 2015/026849 | 2/2015 |
| WO | WO 2015/066344 | 5/2015 |
| WO | WO 2015/193668 | 12/2015 |
| WO | WO 2016/051271 | 4/2016 |
| WO | WO 2016/138138 | 9/2016 |
| WO | WO 2016/205671 | 12/2016 |
| WO | WO 2017/035267 | 3/2017 |
| WO | WO 2017/112702 | 6/2017 |
| WO | WO 2017/122701 | 6/2017 |
| WO | WO 2018/037306 | 3/2018 |
| WO | WO 2018/060732 | 4/2018 |
| WO | WO 2018/206924 | 11/2018 |
| WO | WO 2019/067405 | 4/2019 |
| WO | WO 2019/067413 | 4/2019 |
| WO | WO 2019/067419 | 4/2019 |
| WO | WO 2019/204593 | 10/2019 |
| WO | WO 2019/216919 | 11/2019 |
| WO | WO 2019/241005 | 12/2019 |
| WO | WO 2020/014075 | 1/2020 |
| WO | WO 2020/105005 | 5/2020 |
| WO | WO 2020/112460 | 6/2020 |
| WO | WO 2020/176276 | 9/2020 |
| WO | WO 2021/156437 | 8/2021 |
| WO | WO 2022/013425 | 1/2022 |
| WO | WO 2022/069489 | 4/2022 |

OTHER PUBLICATIONS

Pottkämper et al., "The postictal state—What do we know?", 2020, Epilepsia, 61(6), pp. 1045-1061. (DOI: 10.1111/epi.16519) (Year : 2020).*

Tupal et al., "Serotonin 5-HT4 receptors playa critical role in the action of fenfluramine to block seizure-induced sudden death in a mouse model of SUDEP", 2021, Epilepsy Research, 177, pp. 1-8. (doi.org/10.1016/j.eplepsyres.2021.106777) (Year: 2021).*

Fisher et al., "Definition of the postictal state: When does it start and end?", 2010, Epilepsy & Behavior, 19(2), pp. 100-104. (doi: 10.1016/j.yebeh.2010.06.038) (Year: 2010).*

Debopam Samanta, "Changing Landscape of Dravet Syndrome Management: An Overview", 2020, Neuropediatrics, 51(2), pp. 135-145. (doi.org/10.1055/s-0040-1701694) (Year: 2020).*

Babken Asatryan, "Challenges in Decoding Sudden Unexpected Death in Epilepsy: The Intersection Between Heart and Brain in Epilepsy", 2021, J. Am. Heart Assoc., 10(23): e023571, pp. 1-4. (DOI: 10.1161/JAHA.121 .023571). (Year: 2021).*

Inoue et al., "Stiripentol open study in Japanese patients with Dravet Syndrome" Epilepsia, 50(11):2362-2368 (2009).

Van Rijckevorsel, Kenou, "Treatment of Lennox-Gastaut syndrome: overview and recent findings" Neuropsychiatric Disease and Treatment, 4(6):1001-1019 (2008).

Anandam, R., Affiliations Indian Journal of Pediatrics (Jan. 1, 2000) 67 (1 Suppl):S88-91 (Abstract Only).

Anonymous, "Determination That Pondimin (Fenfluramine Hydrochloride) Tablets, 20 Milligrams and 60 Milligrams, and Ponderex (Fenfluramine Hydrochloride) Capsules, 20 Milligrams Were Withdrawn From Sale for Reasons of Safety or Effectiveness", Federal Register, (Sep. 29, 2015).

Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

Arzimanoglou, "Dravet syndrome: From electroclinical characteristics to molecular biology" Epilepsia, 50(Suppl. 8):3-9 (2009).

Boel and Casaer, "Add-on Therapy of Fenfluramine in Intractable Self-Induced Epilepsy" Neuropaediatrics 1996, 27(4):171-173.

Brunklaus et al., "Prognostic, clinical and demographic features in SCN1A mutation-positive Dravet syndrome" Brain, 2012, p. 1-8.

Brunklaus et al., "Dravet syndrome—From epileptic encephalopathy to channelopathy" Epilepsia (May 16, 2014) 55(7):979-984.

Buchanan, Gordon F. et al., Serotonin neurones have anticonvulsant effects and reduce seizure-induced mortality, The Journal of Physiology, 2014, vol. 592, Issue 19, p. 4395-4410.

Carvalho et al., "d-Amphetamine Interaction with Glutathione in Freshly Isolated Rat Hepatocytes" Chemical Research in Toxicology (Jan. 1996) 9(6):1031-1036.

Casaer et al., "Fenfluramine as a Potential Antiepileptic Drug" Epilepsia, 43(2), 205-206, 2002.

C. B. Catarino et al. "Dravet Syndrome as epileptic encephalopathy: Evidence from long-term course and neuropathology", Brain, vol. 134, No. 10 (Jun. 29, 2011) pp. 2982-3010.

Ceulemans et al., "Poster presented at the 69$^{th}$ Annual Meeting of the American Epilepsy Society" (Dec. 2015) Philadelphia.

Ceulemans et al., "Successful use of fenfluramine as an add-on treatment for Dravet syndrome" Epilepsia, 53(7), 2012, 1131-1139.

Ceulemans, "Overall management of patients with Dravet syndrome" Developmental Medicine & Child Neurology, 2011, 53, 19-23.

Ceulemans B. et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).

Ceulemans B., "Successful Use of Fenfluramine as Add-On Treatment in Dravet Syndrome" Epilepsia, 52(Suppl. 6):4-22 (2011).

Ceulemans et al., "Five-year extended follow-up status of 10 patients with Dravet syndrome treated with fenfluramine" Epilepsia (May 20, 2016) 57(7):e129-e134.

Chiron et al., "The pharmacologic treatment of Dravet syndrome" Epilepsia (2011) 52(Suppl 2):72-75.

Clemens B., "Dopamine agonist treatment of self-induced pattern-sensitive epilepsy. A case Report" Epilepsy Res. 2. 1988, p. 340-343.

Curzon et al., "Appetite suppression by commonly used drugs depends on 5-HT receptors but not on 5-HT availability" TIPS (1997) 18:21-25.

Devinsky et al., "Trial of Cannabidiol for Drug-Resistant Seizures in the Dravet Syndrome" The New Engalnd Journal of Medicine (May 25, 2017) 376(21):2011-2020.

C. Doege et al., "Myoclonic-astatic epilepsy: Doose-Syndrum 2014: Doose syndrome 2014", Zeitschrift FR Epileptologie, (Mar. 20, 2014).

Döring et al. "Thirty Years of Orphan Drug Legislation and the Development of Drugs to Treat Rare Seizure Conditions: A Cross Sectional Analysis" PLOS One, pp. 1-15 (Aug. 24, 2016).

Franco-Perez, Javier "The Selective Serotonin Reuptake Inhibitors: Antidepressants with Anticonvulsant Effects?" Ann Depress Anxiety (2014) 1(5):1025 (2 pages).

Gastaut et al., "Compulsive respiratory sterotypies in children with autistic features: Polygraphic recording and treatment with fenfluramine" Journal of Autism and Developmental Disorders, (Sep. 1, 1987) 17(3):391-406.

K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 925-928.

Gharedaghi et al., "The role of different serotonin receptor subtypes in seizure susceptibility" Exp. Brain Res (2014) 232:347-367.

(56) References Cited

OTHER PUBLICATIONS

Gioia et al., "Confirmatory Factor Analysis of the Behavior Rating Inventory of Executive Function (BRIEF) in a Clinical Sample" Child Neuropsychology (2002) 8(4):249-57.

Habibi et al., "The Impact of Psychoactive Drugs on Seizures and Antiepileptic Drugs" Current Neurology and Neuroscience Reports (Jun. 17, 2016) 16(8):1-10.

Haritos et al., "Metabolism of dexfenfluramine in human liver microsomes and by recombinant enzymes: Role of CYP2D6 and 1A2" Pharmcogenetics (Oct. 1998) 8(5):423-432.

Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se . . . ).

Hazai et al., "Reduction of toxic metabolite formation of acetaminophen" Biochemical and Biophysical Research Communications (Mar. 8, 2002) 291 (4):1089-1094.

Hegadoren et al., "Interactions of iprindole with fenfluramine metabolism in rat brain and liver" Journal of Psychiatry & Neuroscience (Mar. 1991) pp. 5-11.

Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.

Katholieke Universiteit Leuven, University Hospital Antwerp: "Interim results of a fenfluramine open-label extension study", European Patent Register (May 25, 2017).

Klein, M. T. and Teitler, M. , Distribution of 5-htlE receptors in the mammalian brain and cerebral vasculature: an immunohistochemical and pharmacological study, British Journal of Pharmacology, Jun. 2012, vol. 166, No. 4, p. 1290-1302.

Lagae et al. "A pilot, open-label study of the effectiveness and tolerability of low-dose ZX008 (fenfluramine HC1) in Lennox-Gastaut syndrome" Epilepsia (2018) 59: 1881-1888.

Leit, Silvana et al., Design and synthesis of tryptamine-based 5HT2C agonists for the treatment of certain CNS disorders, Division of Medicinal Chemistry Scientific Abstracts for the 240th National ACS Meeting and Exposition, Jul. 28, 2010, MEDI367.

LeJeune et al., "Psychometric Support for an Abbreviated Version of the Behavior Rating Inventory of Executive Function (BRIEF) Parent Form" Child Neuropsychology (2010 16:182-201.

Lopez-Meraz et al., "5-$HT_{1A}$ receptor agonist modify epileptic seizures in three experimental models in rats" Neuropharmacology (2005) 49:367-375.

Martin, et al., "An Examination of the Mechanism of Action of Fenfluramine in Dravet Syndrome: A Look Beyond Serotonin" Presented as part of the Zogenix Scientific Exhibit During the 70$^{th}$ Annual Meeting of the American Epilepsy Society, Houston, Texas (Dec. 2-6, 2016).

Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.

Mudigoudar et al., "Emerging Antiepileptic Drugs for Severe Pediatric Epilepsies" Seminars in Pediatric Neurology (Jun. 2016) 23(2):167-179.

Mulley et al., "SCN1A Mutations and Epilepsy" Human Mutation (2005) 25:535-542.

Naithani et al., "The Conventional Antiepileptic Drug Use When Compared to a Combination Therapy Regime in a Teaching Hospital in India" International Journal of Pharma and Bio Sciences (2012) 3(1):B-191-B-197.

NCT02682927 (Sep. 3, 2016, 10 pages) Accessed from https://www.clinicaltrials.gov/ct2/history/NCT02682927?V=View#StudyPageTop on Mar. 18, 2019).

Nozulak et al., "(+)-cis-4,5,7a,8,9,10,11,11a-Octahydro-7H-10-methylindolo[1,7-bc][2,6]-naphthridine: A 5-$HT_{2C/2B}$ Receptor Antagonist with Low 5-$HT_{2A}$ Receptor Affinity" J. Med. Chem. (1995) 38:28-33.

O'Neill et al., "GR46611 potentiates 5-$HT_{1A}$ receptor-mediated locomotor activity in the guinea pig" European Journal of Pharmacology (1999) 370:85-92.

Pirincci et al., "The Effects of Fefluramine on Blood and Tissue Seratonin (5-Hydroxytryptamine) Levels in Rats" Turk J Vet Anim Sci (2005) 29:857-863.

Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.

Remington, "The Science and Practice of Pharmacy", Nineteenth Edition (1995), pp. 710-712.

Rho, Jong M. "Basic Science Behind the Catastrophic Epilepsies" Epilepsia (2004) 45(Suppl.5):5-11.

Rothman et al., "Serotonergic drugs and valvular heart disease" Expert Opinion on Drug Safety (May 2009) 8(3):317-329.

Schoonjans, An-Sofie "Low-dose fenfluramine in the treatment of neurologic disorders: experience in Dravet syndrome" Therapeutic Advances in Neurological Disorders (Jan. 1, 2015) pp. 328-338.

Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.

Sharma et al. Indian Journal of Pharmacology, 1996, 28(1), 1-10.

Sourbron et al., "Serotonergic Modulation as Effective Treatment for Dravet Syndrome in Zebrafish Mutant Model" ACS Chemical Neuroscience (Feb. 17, 2016) 7(5):588-598.

Sullivan et al. "Effext of ZX008 (fenfluramine HC1 oral solution) on total seizures in Dravet syndrome" Neurology: Official Journal of the American Academy of Neurology, 2018, 90(24):e2187-e2811.

Vickers et al., "Oral Administration of the 5-HT2C receptor agonist, mCPP, reduces body weight gain in rats over 28 days as a result of maintained hypophagia" Psychopharmacology (May 2003), 167 (3): 274-280.

Viola et al., "The Behavior Rating Inventory of Executive Function (BRIEF) to Identify Pediatric Acute Lymphoblastic Leukemia (ALL) Survivors At Risk for Neurocognitive Impairment" Journal of Pediatric Hematology/Oncology (Apr. 1, 2017) 39(3):174-178.

Wirrell et al., "Stiripentol in Dravet syndrome: Results of a retrospective U.S. study" Epilepsia (2013) 54(9):1595-1604.

Wirrell et al., "Optimizing the Diagnosis and Management of Dravet Syndrome: Recommendations From a North American Consensus Panel" Pediatric Neurology (Mar. 2017) 68:18-34.

Wurtman et al., "Fenfluramine and other serotoninergic drugs depress food intake and carbohydrate consumption while sparing protein consumption" Current Medical Research and Opinion (1979) 6(1 Supp):28-33.

Yamaori et al., "Potent inhibition of human cytochrome P450 3A isoforms by cannabidiol: Role of phenolic hydroxyl groups in the resorcinol moiety" Life Sciences (2011) 88:730-736.

Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.

Zhang et al., *A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS)*. Presented at the 2016 American Conference for Pharmacokinetics.

Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts accepted for American Conference on Pharmacometrics 2016 (ACoP7).

Zhang et al., "Pharmacological Characterization of an Antisense Knockdown Zebrafish Model of Dravet Syndrome: Inhibition of Epileptic Seizures by the Serotonin Agonist Fenfluramine" PLOS One (May 12, 2015) 10(5)::16-17 (Abstract).

Zhuang et al. (2016), "PBPK modeling and simulation in drug research and development" in Acta Pharmaceutica Sinica B 2016;6(5):430-440.

Zogenix "Corporate Update Nasdaq: ZGNX" (Jun. 1, 2016) Retrieved from the Internet: URL:http://www.jefferies.com/CMSFiles/Jefferies.com/files/Conferences/060716/Presentations/Zogenix%20Inc.pdf [retrieved on Feb. 21, 2018].

(56) References Cited

OTHER PUBLICATIONS

F Brenot et al., "Primary Pulmonary Hypertension and Fenfluramine Use.", Heart, vol. 70, No. 6, Dec. 1, 1993 (Dec. 1, 1993), pp. 537-541.
Favale et al., "The anticonvulsant effect of citalopram as indirect evidence of serotonergic impairment in human epileptogenesis" Seizure (2003) 12:316-319.
Jake Remaly: "Fenfluramine Reduces Convulsive Seizure Frequency in Dravet Syndrome. Epilepsy Resource Center", Jan. 1, 2018 (Jan. 1, 2018).
An-Sofie Schoonjans et al: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.
Faingold et al., "Prevention of seizure-induced sudden death in a chronic SUDEP model by semichronic administration of a selective serotonin reuptake inhibitor" Epilepsy & Behavior (2011) 22:186-190.
Manzke et al., "5-HT4(a) receptors avert opiod-induced breathing depression without loss of analgesia" Science (Jul. 11, 2003) 301:226-229.
Wallace et al., "Pharmacotherapy for Dravet Syndrome" Paediatr. Drugs, 18(3):197-208 (Jun. 2016).
Wirrell et al., "Stiripentol in Dravet Syndrome: Is it Worth It?" Epilepsy Currents, 14(1):22-23 (Jan./Feb. 2014).
Wirrell et al., "Treatment of Dravet Syndrome" Can. J. Neurol. Sci., 43(Suppl. 3):S13-18 (Jun. 2016).
Anonymous, "Health Technology Briefing: Fenfluramine hydrochloride for treatment of seizures associated with Lennox-Gastaut syndrome" NIHR Innovation Observatory (May 2019) 8 pages.
Anonymous "Zogenix Announces Positive Top-Line Results from Global Pivotal Phase 3 Trial of FINTEPLA for the treatment of Lennox-Gastaut Syndrome" Bio Space (Feb. 6, 2020) pp. 1-12.
Baker, M. "Zogenix Completes Enrollment in Phase 3 Trial of FINTELPLA in Lennox-Gastaut Syndrome" (Jul. 8, 2019) 2 pages.
Anonymous "Selective Serotonin reuptake Inhibitor—Wikipedia" Internet https://en.wikipedia.org/wiki/Selective_serotonin_reuptake_inhibitor (Feb. 1, 2020 (retrived on Feb. 4, 2020)).
Klein et al., "Cannabidiol potentiates Delta$^9$-tetrahydrocannabinol (THC) behavioural effects and alters THC pharmacokinetics during acute and chronic treatment in adolescent rats" Psychopharmacology (2011) 218:443-457.
Slick et al., "Frequency of Scale Elevations and Factor Structure of the Behavior Rating Inventory of Executive Function (Brief) in Children and Adolescents with Intractiable Epilepsy" Child Neuropsychology (2006) 12:181-189.
ONFI Prescribing Information. Lundbeck, Deerfield, Reference ID: 4028780 [online], Dec. 2016, [retrieved on Jun. 22, 2021, <URL: https://www.accessdata.fda.gov/drugsatfda_docs/label/2016/203993s005lbl.pdf>.
Study NCT02926898 on Date: May 1, 2017 (v6), ClinicalTrials.gov archive [online], May 1, 2017, [retrieved on Jun. 22, 2021], <URL: https://clinicaltrials.gov/ct2/history/NCT02926898>.
Zaccara et al., "Interactions between antiepileptic drugs, and between antiepileptic drugs and other drugs" Seminar in Epileptology (2014) 16(4):409-432.
Aras et al., "The European patient with Dravet Syndrome: Results from a parent-reported survey on antiepileptic drug use in the European population with Dravet Syndrome" Epilepsy & Behavior (2015) 44:104-109.
Clinical Trials ClinicalTrials.gov Identifier: NCT02224560 (Jul. 27, 2018).
Russo et al., "Agonistic Properties of Cannabidiol at 5-HT1a Receptors" Neurochemical Research (2005) 30(8):1037-1043.
Dravet, Charlotte, "The core Dravet syndrome phenotype" Epilepsia, 52(Supp. 2):3-9 (2011).
Selmer et al., "SCN1A mutation screening in adult patients with Lenox-Gastaut syndrome features" Epilepsy & Behavior (Nov. 1, 2009) 16(3):555-57.

Kelley et al., "Doose syndrome (myoclonic-astatic epilepsy): 40 years of progress" Developmental Medicine & Child Neurology (2010) 52(11):988-993.
McTague et al., "The genetic landscape of the epileptic encephalopathies of infancy and childhood" Lancet Neurol. (2016) 15:304-316.
Oguni et al., "Treatment and Long-Term Prognosis of Myoclonic-Astatic Epilepsy of Early Childhood," Neuropediatrics (2002) 33(3):122-32.
Bagdy et al., "Serotonin and epilepsy," J. Neurochem., 100:857-73 (2007).
Ceulemans et al., "Clinical Correlations of Mutations in the SCN1A Gene: From Febrile Seizures to Severe Myoclonic Epilepsy in Infancy" Pediatr. Neurol. 30(4):236-43 (2004).
Coleman et al., "Monitoring for adverse drug reactions," Br. J. Clin. Pharmacol., 61(4):371-78 (2006).
"Diacomit: EPAR—Scientific Discussion," European Medicines Agency ("EPAR Diacomit") https://www/ema/europa.eu/en/documents/scientific-discussion/diacomit-epar-scientific-discussion_en.pdf, published 2009.
Ferretti et al., "Direct High-performance liquid chromatograph resolution on a chiral column of dexfenfluramine and its impurities, in bulk raw drug and pharmaceutical formulations" J. Chromatogr. A. 731:340-45 (1996).
Gordon et al., "A SARS-CoV-2 protection interaction map reveals targets for drug repurposing" Nature (Apr. 30, 2020) 583(7816:459-468.
Haute Autorité de Santé (HAS), French National Authority for Health, issued an opinion on Diacomit ("HAS Opinion") https://www.has-sante.ir/upload/dox/application/pdf/2010-01/diacomit_ct_4347.pdf (Jun. 6, 2007).
Heisler et al., "Epilepsy and Obesity in Serotonin 5-HT$_{2C}$ Receptor Mutant Mice," Ann. NY Acad. Sci. 861:74-78 (1998).
International Conference On Harmonisation Of Technical Requirements for Registration of Pharmaceuticals for Human Use, "ICH Harmonised Tripartite Guidline: Impurities in New Drug Substances," Q3A(R2) (2006).
Jingyu et al., "Study on Synthesis of Amphetamine Compounds" Chem J. of Chinese Univ., 9(2), 12 pages (1988).
Martin et al., "Fenfluramine acts as a positive modulator of sigma-1 receptors" Epilepsy and Behavior, Academic Press, San Diego, CA, US (Mar. 10, 2020) 105:1-9.
Mathews et al., "Effect of D-Fenfluramine on the Lymphocyte Response of HIV+ Humans" International Journal of Immunopharmacology (Jan. 1, 1998) 20:751-763.
Olson et al., "Cyclin-Dependent Kinase-Like 5 Deficiency Disorder: Clinical Review" Pediatric Neurology (2019) 97:18-25.
Public Law 110-85, 110$^{th}$ Congress ("FDA Amendments Act of 2007") published 2007.
Rothman et al., "(+)-Fenfluramine and Its Major Metabolite, (+)-Norfenfluramine, Are Potent Substrates for Norepinephrine Transporters," J. Pharmacol. Exp. Ther., 305(3):1191-99 (2003).
Scala et al., "CDKL5/STK9 is mutated in Rett syndrome variant with infantile spasms" J Med Genet (2005) 42:103-107.
Tran et al., "Dakin-West Synthesis of β-Aryl Ketones" J. Org. Chem. (2006) 71:6640-6643.
Vela, Jose Miguel "Repurposing Sigma-1 Receptor Ligands for COVID-19 Therapy?" Frontiers in Pharmacology (Nov. 9, 2020) 11:1-23.
Wee et al., "Risk for Valvular Heart Disease among Users of Fenfluramine and Dexfenfluramine Who Underwent Echocardiography before Use of Medication," Annals of Internal Medicine, 129(11):870-874 (1998).
Archer et al., "Primary Pulmonary Hypertension, A Vascular Biology and Translational Research "Work in Progress"" Clinical Cardiology: New Frontiers, Circulation, 102:2781-2791 (Nov. 28, 2000).
Echocardiogram, Echocardiogram Test for Pulmonary Arterial Hypertension PAH (https://pulmonaryhypertensionm.com/echocardiogram/) pp. 1-5 (Jan. 4, 2012).
FDA-approved Treatments for Pulmonary Hypertension, Vera Moulton Wall Center for Pulmonary Vascular Diseases, Stanford (https://med.stanford.edu/wallcenter/patient-resources/fda.html) pp. 1-8 (Jan. 19, 2017).

(56) References Cited

OTHER PUBLICATIONS

Gardner, Amanda "Living Your Best With Pulmonary Hypertension" WebMD, pp. 1-5 (Jan. 2, 2019).
Khan et al., "Epileptic Encephalopathies: An Overview" Epilepsy Research and Treatment, vol. 2012, pp. 1-8 (Sep. 12, 2012).
Mari et al., "CDKL5 belongs to the same molecular pathway of MeCP2 and it is responsible for the early-onset seizure variant of Rett syndrome" Human Molecular Genetics (2005) 14(14):1935-1946.
Pulmonary Hypertension and Edema, (pulmonaryhypertensionnews.com/pulmonary-hypertension-and-edema/) pp. 1-3 (Nov. 9, 2015).
Scheffer et al., "ILAE classification of the epilepsies: Position paper of the ILAE Commission for Classification and Terminology" Epilepsia (2017) 58)4):512-521.
Specchio et al., "International League Against Epilepsy classification and definition of epilepsy syndromes with onset in childhood: Position paper by the ILAE Task Force on Nosology and Definitions" Epilepsia (Mar. 17, 2022) 00:1-45.
Weir et al., "Anorexic Agents Aminorex, Fenfluramine, and Dexfenfluramine Inhibit Potassium Current in Rat Pulmonary Vascular Smooth Muscle and Cause Pulmonary Vasoconstriction" American Heart Association, Circulation, 94(9):2216-2220 (Nov. 1996).
Zuberi et al., "Commentary: A New Classification is Born" International League Against Epilepsy (2017) pp. 511.
Aicardi et al., "Treatment of Self-Induced Photosensitive Epilepsy with Fenfluramine" New England Journal of Medicine (1985) 313:1419.
Aicardi et al., "Syncopal Attacks Compulsively Self-induced by Valsalva's Maneuver Associated with Typical Absence Seizures" Archives of Neurology (1988) 45:923-925.
Bird et al., "Combination of pharmaceutical compositions for treatment of neurological disorders" STN International (Columbus, Ohio) HCAPLUS database, Accession No. 2013:83254 (2013).
Coma et al., "New combination therapies for treating neurological dissorders" STN International (Columbus, Ohio) HCAPLUS database, Accession No. 2013:682383 (2013).
Cozzi et al., "Indan Analogs of Fenfluramine and Norfenfluramine Have Reduced Neurtoxic Potential" Pharmacology Biochemistry and Behavior (1998) 59(3):709-715.
Dimpfel et al., "Hesperidin and hesperetin for the treatment of epilepsy migraine, schizophrenia, depression, and drug abuse" STN International (Columbus, Ohio) HCAPLUS database, Accession No. 2006:1205690 (2006).
Droogmans et al., "Role of echocardiography in tox heart vavulopathy" European Journal of Echocardiography, 10:467-476 (2009).
File History of U.S. Pat. No. 9,549,909 issued on Jan. 24, 2018 (571 pp).
File History of U.S. Pat. No. 9,603,815 issued on Mar. 28, 2017 (385 pp).
File History of U.S. Pat. No. 9,603,814 issued on Mar. 28, 2017 (466 pp).
File History of U.S. Pat. No. 9,610,260 issued on Apr. 4, 2017 (371 pp).
File History of U.S. Pat. No. 10,478,441 issued on Nov. 19, 2019 (761 pp).
File History of U.S. Pat. No. 10,478,442 issued on Nov. 19, 2019 (980 pp).
File History of U.S. Appl. No. 14/447,369, filed Jul. 30, 2014 (now abandoned) (285 pp.).
File History of U.S. Appl. No. 15/429,650, filed Feb. 10, 2017 (now abandoned) (267 pp).
File History of U.S. Appl. No. 15/429,641, filed Feb. 10, 2017 (now abandoned) (285 pp).
File History of U.S. Appl. No. 15/429,506, filed Feb. 10, 2017 (now abandoned) (641 pp).
File History of U.S. Appl. No. 16/596,166, filed Oct. 8, 2019 (now abandoned) (123 pp).
File History of U.S. Appl. No. 16/869,284, filed May 7, 2020 (now abandoned) (42 pp).
File History of U.S. Appl. No. 16/909,055, filed Jun. 12, 2020 (pending) (85 pp).
File History of U.S. Pat. No. 10,351,509 issued Jul. 16, 2019 (226 pp).
File History of U.S. Pat. No. 10,351,510 issued Jul. 16, 2019 (244 pp).
File History of U.S. Pat. No. 10,947,183 issued Mar. 16, 2021 (293 pp).
Garone et al., "Deoxypyrimidine monophosphate bypass therapy for thymidine kinase 2 deficiency" EMBO Molecular Medicine Aug. 1, 2014) 6(8):1016-1027.
Gross et al., "The influence of the sparteine/debrisoquine genetic polymorphism on the disposition of dexfenfluramine" Br J Clin Pharmacol (1996) 41:311-317.
Hattori et al., "A Screening test for the prediction of Dravet Syndrome before one year of age" Epilepsia (Apr. 2008) 49(4):626-633.
Hawkins et al., "Synthesis of [14C] Fenfluramine and [14C]-S780" Journal of Labelled Compounds (1974) 10(4):63-670.
Hirayama, Noriaki, Organic Compound Crystallization Handbook: Principles and Know-How (Maruzen, Co., Ltd.), Jul. 25, 2008, pp. 57-84.
Ji et al., "Study of Fenfluramine Synthesis Route" Journal of Shenyang College of Pharmacy (Apr. 1994) 11 (2):116-118.
Kaiser et al., "Synthesis and Anorectic Activity o Some 1-Benzylcyclopropylamines" Journal of Medicinal Chemistry, American Chemical Society, US (1970) 13(5):820-826.
Lambert et al., "Inductive Enhancement of Aryl Participation" Journal of the American Chemical Society (Apr. 27, 1977) 99(9):3059-67.
Lewis et al., "Biosynthesis of Canescin, a Metabolite of *Aspergillus malignus*: Incorporation of Methionine, Acetate, Succinate, and Isocoumarin Precursors, Labelled with Deuterium and Carbon-13" J. Chem. Soc. Perkin Trans I (1988) pp. 747-754.
LoPinto-Khoury et al., "Antiepileptic Drugs and Markers of Vascular Risk" Curr Treat Options Neurol (Jul. 2010) 12(4):300-308.
Patani et al;, "Bioisosterism: A Rational Approach to Drug Design" Chem. Rev. (1996) 96:3147-3176.
Porra et al., "Determination of Fenfluramine Enantiomers in Pharmaceutical Formulations by Capillary Zone Electrophoresis" Chromatographia (Oct. 1995) 41(7/8):383-388.
Registry(STN) [online], Jun. 7, 2015, [Retrieval Date: Sep. 28, 2020], CAS Registry No. 1775169-27-1.
Su et al., "The Synthesis of 2-Amino-1-Penylpropanes" Chemical Journal of Chinese Universities (1988) 9(2):134-139.
Van Der Steldt et al., "The Effect of Alkyl Substitution in Drugs" Arzneimittelforschung—Drug Research (1965) 15:1251-1253.
Vivero et al., "A close look at fenfluramine and dexfenfluramine" The Journal of Emergency Medicine (1998) 16(2):197-205.
Werbel et al., "Synthesis, Antimalarial Activity, and Quantitative Structure-Activity Relationships of Tebuquine and a Series of Related 5-[(7-Chloro-4-quinolinyl)amino]-3[(alkylamino)methyl][1,1'-biphenyl]-2-ols and N omega-Oxides" J. Med. Chem. (1986) 29:924-939.

* cited by examiner

Fig. 1C

% Protection against AGS2 vs Log (FFA dose, mg/kg)

$ED_{50} = 1.33673$ (21.71 mg/kg)

Figs. 4A and 4B
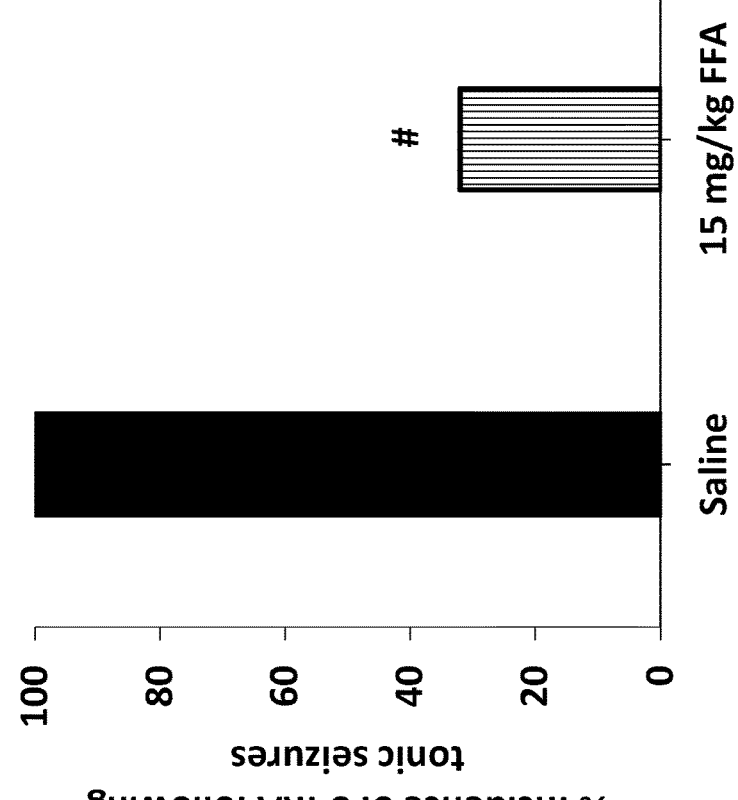
Fig. 4B
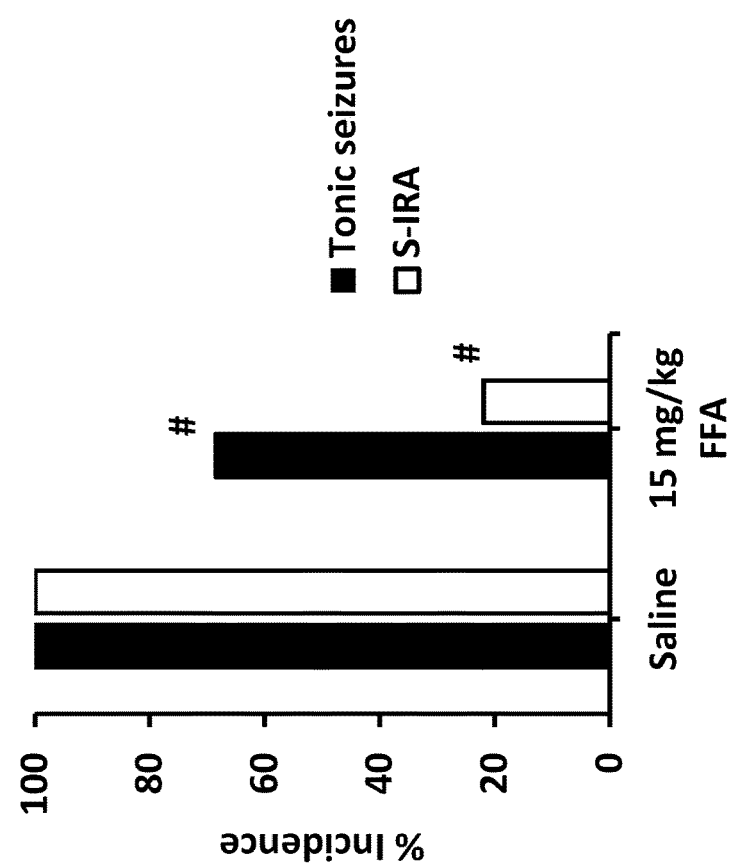
Fig. 4A

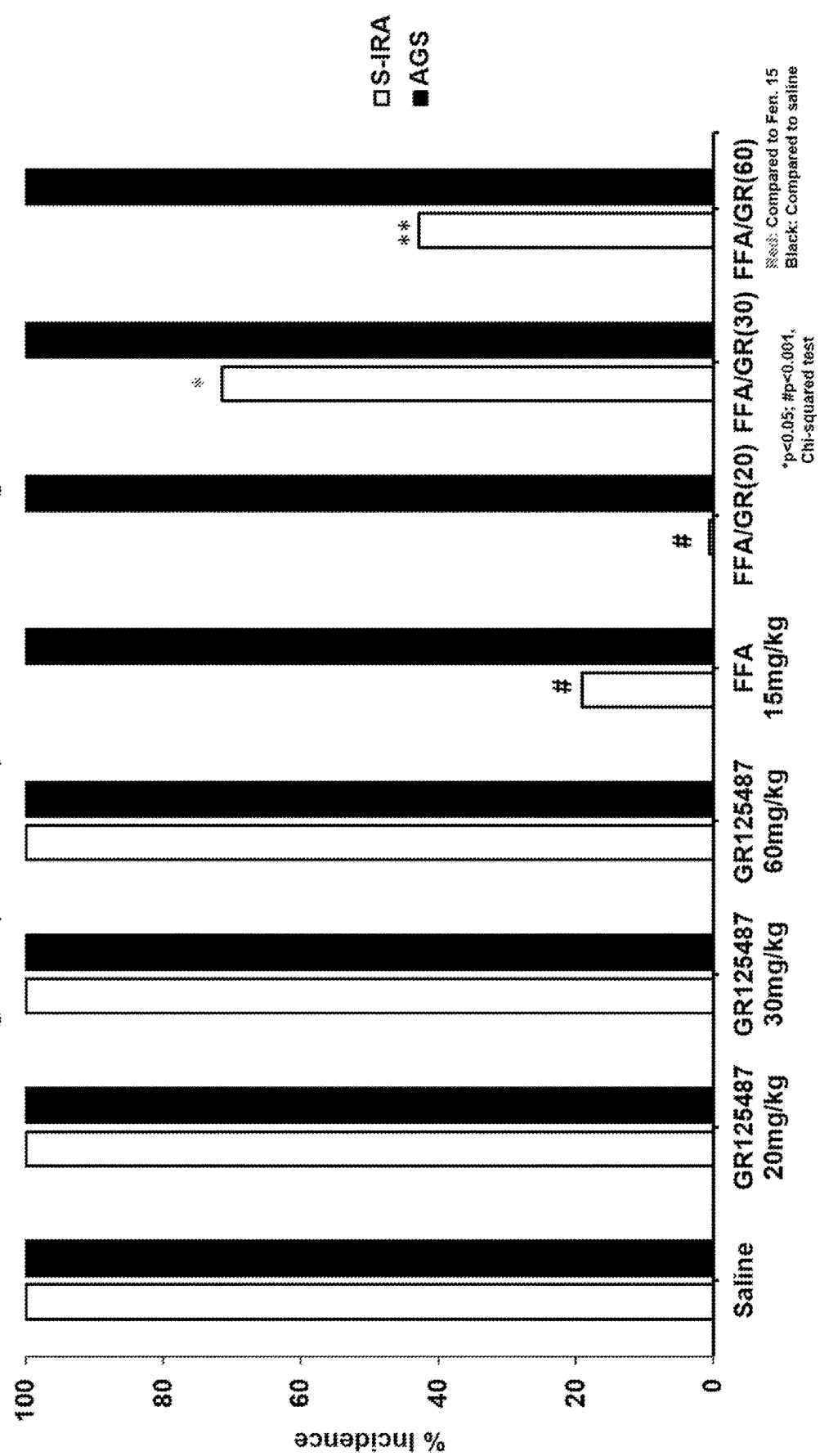

COMPOSITIONS AND METHODS FOR TREATING SEIZURE-INDUCED SUDDEN DEATH

FIELD

The present invention relates generally to the therapeutic treatment of patients diagnosed with a seizure disorder such as epilepsy or epileptic encephalopathy. More specifically, the invention relates to the use of fenfluramine as a therapeutic agent, and to methods of its use to treat human patients diagnosed with intractable forms of epilepsy or epileptic encephalopathy and at risk of seizure-induced Sudden Unexpected Death in Epilepsy (SUDEP).

INTRODUCTION

Epilepsy is a condition of the brain marked by a susceptibility to recurrent seizures. There are numerous causes of epilepsy including, but not limited to birth trauma, perinatal infection, anoxia, infectious diseases, ingestion of toxins, tumors of the brain, inherited disorders or degenerative disease, head injury or trauma, metabolic disorders, cerebrovascular accident and alcohol withdrawal.

A large number of subtypes of epilepsy have been characterized, each with its own unique clinical symptoms, signs, and phenotype, underlying pathophysiology and distinct responses to different treatments. The most recent version, and the one that is widely accepted in the art, is the system adopted by the International League Against Epilepsy's ("ILAE") Commission on Classification and Terminology (See e.g., Berg et. al, "Revised terminology and concepts for organization of seizures," *Epilepsia,* 51(4):676-685 (2010)):

TABLE 1

| ILAE Classification Scheme for Epilepsy Subtypes | |
|---|---|
| I. ELECTROCHEMICAL SYNDROMES (by age of onset) | |
| A. Neonatal period | 1. Benign familial neonatal epilepsy (BFNE) |
| | 2. Early myoclonic encephalopathy (EME) |
| | 3. Ohtahara syndrome |
| B. Infancy | 1. Epilepsy of infancy with migrating focal seizures |
| | 2. West syndrome |
| | 3. Myoclonic epilepsy in infancy (MEI) |
| | 4. Benign infantile epilepsy |
| | 5. Benign familial infantile epilepsy |
| | 6. Dravet syndrome |
| | 7. Myoclonic encephalopathy in non-progressive disorders |
| C. Childhood | 1. Febrile seizures plus (FS+) (can start in infancy) |
| | 2. Panayiotopoulos syndrome |
| | 3. Epilepsy with myoclonic atonic (previously astatic) seizures (Doose syndrome) |
| | 4. Benign epilepsy with centrotemporal spikes (BECTS) |
| | 5. Autosomal-dominant nocturnal frontal lobe epilepsy (ADNFLE) |
| | 6. Late onset childhood occipital epilepsy (Gastaut type) |
| | 7. Epilepsy with myoclonic absences |
| | 8. Lennox-Gastaut syndrome |
| | 9. Epileptic encephalopathy with continuous spike-and-wave during |
| | 10. Landau-Kleffner syndrome (LKS) |
| | 11. Childhood absence epilepsy (CAE) |
| D. Adolescence - Adult | 1. Familial focal epilepsy with variable foci (childhood to adult) |
| | 2. Reflex epilepsies |
| E. Less specific age relationship | 1. Familial focal epilepsy with variable foci (childhood to adult) |
| | 2. Reflex epilepsies |
| II. DISTINCTIVE CONSTELLATIONS | |
| A. Mesial temporal lobe epilepsy with hippocampal sclerosis (MTLE with HS) | |
| B. Rasmussen syndrome | |
| C. Gelastic seizures with hypothalamic hamartoma | |
| D. Hemiconvulsion-hemiplegia-epilepsy | |
| E. Epilepsies that do not fit into any of these diagnostic categories, | 1. Presumed cause (presence or absence of a known structural or metabolic condition) |
| | 2. Primary mode of seizure onset (generalized vs. focal) |
| III. EPILEPSIES ATTRIBUTED TO AND ORGANIZED BY STRUCTURAL-METABOLIC CAUSES | |
| A. Malformations of cortical development (hemimegalencephaly, heterotopias, etc.,) | |
| B. Neurocutaneous syndromes (tuberous sclerosis complex, Sturge-Weber, etc.,) | |
| C. Tumor | |
| D. Infection | |
| E. Trauma | |
| IV. ANGIOMA | |
| A. Perinatal insults | |
| B. Stroke | |
| C. Other causes | |

TABLE 1-continued

ILAE Classification Scheme for Epilepsy Subtypes

V. EPILEPSIES OF UNKNOWN CAUSE
VI. CONDITIONS WITH EPILEPTIC SEIZURES NOT TRADITIONALLY DIAGNOSED AS FORMS OF EPILEPSY PER SE
A. Benign neonatal seizures (BNS)
B. Febrile seizures (FS)

Part V of the ILAE classification scheme underscores the fact that the list is far from complete, and that there are still subtypes of epilepsy or epileptic encephalopathy that have not yet been fully characterized, or that remain unrecognized as distinct syndromes. That is to say, those skilled in the art will recognize that different subtypes of epilepsy are triggered by different stimuli, are controlled by different biological pathways, and have different causes, whether genetic, environmental, and/or due to disease or injury of the brain. In other words, the skilled artisan will recognize that teachings relating to one epileptic subtype are most commonly not necessarily applicable to any other subtype.

Of particular importance is that there are a large number of compounds that are used to treat different types of epilepsy or epileptic encephalopathy, and that different subtypes of epilepsy or epileptic encephalopathy respond differently to different anticonvulsant drugs. That is, while a particular drug can be effective against one form of epilepsy, it can be wholly ineffective against others, or even contraindicated due to exacerbation of symptoms, such as worsening the frequency and severity of the seizures. As a result, efficacy of a particular drug with respect to a particular type of epilepsy is wholly unpredictable, and therefore it is an entirely surprising discovery when a particular drug not previously known to be effective for a particular type of epilepsy or epileptic encephalopathy is found to be effective. This is especially true for those epilepsy syndromes which were previously intractable and resistant to known drugs.

A large number of different drugs have been used in the treatment of various forms of epilepsy or epileptic encephalopathy. Although the list below is not comprehensive, it is believed to include those drugs which are widely prescribed in patients diagnosed with epilepsy.

TABLE 2

Commonly Prescribed Antiepileptic Drugs

| Generic Name | Trade Name |
| --- | --- |
| carbamazepine | Carbatrol, Epitol, Equetro, Tegretol |
| clobazam | Frisium, Onfi |
| clonazepam | Klonopin |
| diazepam | Diastat, Valium |
| ezogabine | Potiga |
| eslicarbazepine acetate | Aptiom |
| ethosuximide | Zarontin |
| felbamate | Felbatol |
| fosphenytoin | Cerebyx |
| gabapentin | Gralise, Horizant, Neurontin, Gabarone |
| Lacosamide | Vimpat |
| lamotrigine | LaMICtal |
| levetiracetam | Elepsia, Keppra, Levetiractam Stavzor |
| lorazepam | Ativan |
| oxcarbazepine | Trileptal, Oxtellar |
| perampanel | Fycompa |
| phenobarbital | Luminal, Solfoton |
| phenytoin | Dilations, Prompt, Di-Phen, Epanutin, Phenytek |
| pregabalin | Lyrica |
| primidone | Mysoline |
| rufinamide | Banzel, Inovelon |

TABLE 2-continued

Commonly Prescribed Antiepileptic Drugs

| Generic Name | Trade Name |
| --- | --- |
| tiagabine | Gabitril |
| topiramate | Qudexy XR, Topamax, Topiragen, Trokendi XR, Depacon, Depakene, Depakote, |
| valproate, valproic acid | |
| vigabatrin | Sabril |
| zonisamide | Zonegran |

Because different subtypes of epilepsy or epileptic encephalopathy respond differently to different anticonvulsant drugs, the efficacy of a particular drug for a particular type of epilepsy or epileptic encephalopathy is in all cases a surprising result.

Dravet Syndrome is a rare and catastrophic form of intractable epilepsy that begins in infancy. Initially, the patient experiences prolonged seizures. In their second year, additional types of seizure begin to occur and this typically coincides with a developmental decline or stagnation, possibly due to repeated cerebral hypoxia resulting from ongoing relentless seizures. This leads to poor development of language and motor skills. Children with Dravet Syndrome are likely to experience multiple seizures per day. Epileptic seizures are far more likely to result in death in sufferers of Dravet Syndrome; approximately 10 to 15% of patients diagnosed with Dravet Syndrome die in childhood, particularly between two and four years of age. Additionally, patients are at risk of numerous associated conditions including orthopedic developmental issues, impaired growth and chronic upper respiratory infections. The cost of care for Dravet Syndrome patients is also high, as affected children require constant supervision and many require institutionalization as they reach teenage years.

The presentation and diagnosis of Dravet syndrome differs significantly from other forms of epilepsy. Ceulemans teaches that Dravet syndrome can be distinguished from other forms of epilepsy by: " . . . the appearance of tonic-clonic seizures during the first year of life, the occurrence of myoclonic seizures and ataxia later, impaired psychomotor development following the onset of the seizures, and poor response to anti-epileptic drugs." (Ceulemans, *Developmental Medicine & Child Neurology,* 2011, 53 (Suppl. 2): 19-23).

Brunklaus et. al, (*BRAIN,* 2012, 135:2329-2336) similarly observes: "Dravet syndrome typically presents in the first year of life with prolonged, febrile and afebrile, generalized clonic or hemiclonic epileptic seizures in children with no pre-existing developmental problems. Other seizure types including myoclonic, focal and atypical absence seizures appear between the ages of 1 and 4 years (Dravet, 1978)."

Thus, the presentation and diagnosis of Dravet syndrome is significantly different from other forms of epilepsy. Given its distinctive clinical nature, one of ordinary skill in the art would therefore not find it obvious or have reason to assume that any particular compound would be efficacious in Dravet syndrome.

Dravet is also distinctive in terms of its genetic aspects. It is known in the art (Ceulemans, *Developmental Medicine & Child Neurology*, 2011, 53 (Suppl. 2): 19-23; Brunklaus et. al, *BRAIN*, 2012, 135:2329-2336) that mutations in the alpha-subunit of the neuron-specific voltage-gated sodium channel (SCN1a) was discovered as the primary genetic cause for Dravet syndrome in 2001. Thus, the cause of Dravet syndrome is significantly different as compared to other forms of epilepsy. Moreover, unlike other forms of epilepsy, diagnosis of Dravet is based in part on detection of these genetic mutations in addition to clinical observation. Consequently, with the advent of improved genetic testing, there has been an increase in the number of patients diagnosed with the disease.

Of particular concern, children with Dravet Syndrome are particularly susceptible to episodes of Status Epilepticus. This severe and intractable condition is categorized as a medical emergency requiring immediate medical intervention, typically involving hospitalization. Status Epilepticus can be fatal. It can also be associated with cerebral hypoxia, possibly leading to damage to brain tissue. Frequent hospitalizations of children with Dravet Syndrome are clearly distressing, not only to the patient but also to family and care givers.

Also of concern to people living with epilepsy is the risk of Sudden Unexpected Death in Epilepsy (SUDEP). SUDEP refers to deaths in people with epilepsy that are not caused by injury, drowning, or other known causes. Although estimates vary, some studies suggest that each year there are about 1.16 cases of SUDEP for every 1,000 people with epilepsy. Most, but not all, cases of SUDEP occur during or immediately after a seizure, and although the exact cause is not known, but the following is a list of factors that may play a role:

Breathing. A seizure may cause a person to have pauses in breathing due to apnea, or to airway obstruction. If these pauses last too long, they can reduce the oxygen in the blood to a life-threatening level. Heart rhythm. A seizure may cause a dangerous heart rhythm or even heart failure. Other causes and mixed causes. SUDEP may result from more than one cause or a combination involving both breathing difficulty and abnormal heart rhythm.

Three drugs that are especially effective for partial onset seizures are vigabatrin, a selective and irreversible GABA-transaminase inhibitor that greatly increases whole-brain levels of GABA; tiagabine, a potent inhibitor of GABA uptake into neurons and glial cells; and topiramate, which is believed to produce its antiepileptic effect through several mechanisms, including modification of $Na^+$-dependent and/or $Ca^{2+}$-dependent action potentials, enhancement of GABA-mediated $Cl^-$ fluxes into neurons, and inhibition of kainate-mediated conductance at glutamate receptors of the AMPA/kainate type. (Ängehagen, et al., 2003, *Neurochemical Research*, 28(2):333-340).

Although a number of anticonvulsant therapies have been employed to reduce the instance of seizures in patients with Dravet Syndrome, the results obtained with such therapies are typically poor and those therapies only affect partial cessation of seizures at best. In general, seizures associated with Dravet Syndrome are typically resistant to conventional treatments, and anticonvulsants whose activity is via blockade of the sodium channel worsen seizures in Dravet syndrome. Further, many anticonvulsants such as clobazam and clonazepam have undesirable side effects, which are particularly acute in pediatric patients.

It has recently been discovered that the intractable seizures characteristic of Dravet syndrome can be significantly reduced in frequency and/or severity, and in some cases eliminated entirely, by administering the drug 3-trifluoromethyl-N-ethylamphetamine (hereinafter "fenfluramine"). See Ceulemans et. al., Successful use of fenfluramine as an add-on treatment for Dravet Syndrome, Epilepsia 53(7): 1131-1139, 2012. Fenfluramine, is an amphetamine derivative having the following structure:

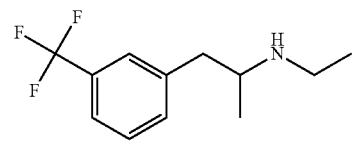

Structure 1
(RS)-N-ethyl-1-[3-(trifluoromethyl)phenyl]propan-2-amine

Fenfluramine is a racemic mixture of two enantiomers, dexfenfluramine and levofenfluramine, and has been reported to increase the circulating levels of serotonin, a neurotransmitter that regulates mood, appetite and other functions.

Serotonin (also known as "5-hydroxytryptamine" or "5-HT") is a monoaminergic neurotransmitter believed to modulate numerous sensory, motor and behavioral processes in the mammalian nervous system. These diverse responses are elicited through the activation of a large family of receptor subtypes. Of the many subtypes of serotonin receptors, the $5-HT_{1B}$ and $5-HT_{2C}$ subtypes are most strongly implicated in modulating feeding and body weight, and these receptors are expressed in hypothalamic regions believed to be involved in food intake regulation. Fenfluramine was known to have high affinity for and activity at the 5-HT2A, $5-HT_{2B}$ and $5-HT_{2C}$ receptor subtypes (Rothman et al, 2015), and because $5-HT_{2C}$-agonists trigger appetite suppression, fenfluramine was used for treating obesity by co-administering it together with phentermine as part of the popular weight loss drug combination treatment marketed as Fen-Phen (i.e., fenfluramine/phentermine). Fen-Phen was first marketed in the US in 1973 to prevent and treat obesity, but in 1997, Fen-Phen was withdrawn from the US and global markets, as its use was associated with the onset of cardiac valvulopathy and pulmonary hypertension.

The adverse effects associated with the use of Fen-Phen as an anorexic agent were believed to be attributable to the interaction of fenfluramine's primary metabolite norfenfluramine with the $5-HT_{2B}$ receptor, the activation of which was associated with cardiac valvulopathy. It was for this reason that Fen-Phen was withdrawn from the market and is no longer indicated for use in any therapeutic area.

Despite past cardiovascular safety concerns that arose when high doses of fenfluramine were used for treatment of adult obesity, attempts have been made to identify further therapeutic uses for that product, while weighing the known cardiovascular risks of fenfluramine against potential therapeutic benefits. One disorder for which new treatment options are sorely needed is epilepsy or epileptic encephalopathy.

Although some antiepileptic drugs have been developed, approximately one third of patients with epilepsy are refractory to treatment. Therefore, the search for new mechanisms and medications that can regulate cellular excitability continues.

Historically, investigation of fenfluramine's efficacy in epilepsy patients led to a common paradigm, i.e., that fenfluramine's primary effects were on behaviors that caused or induced seizures, not treating or preventing the seizure itself. For example, Aicardi and Gastaut (*New England Journal of Medicine* (1985), 313:1419 and *Archives of Neurology* (1988) 45:923-925) reported four cases of self-induced photosensitive seizures, i.e., seizures caused by patients purposely staring into bright lights or the sun, which were found to respond to treatment with fenfluramine. Similarly, Clemens, in *Epilepsy Research* (1988) 2:340-343, reported a case study wherein a boy suffering pattern sensitivity-induced seizures that were resistant to anticonvulsive treatment was treated with fenfluramine to curb the patient's compulsive seizure-inducing behavior. Fenfluramine reportedly successfully terminated these self-induced seizures. Clemens concluded that this was because fenfluramine blocked the photosensitive triggering mechanism, and, secondarily, by diminishing the pathological drive toward the seizure triggering behavior/compulsion, i.e., not by treating the seizure itself.

In *Neuropaediatrics*, (1996); 27(4):171-173, Boel and Casaer reported on a study on the effects of fenfluramine on children with refractory epilepsy, all of whom exhibited compulsive seizure-inducing behavior. They observed that when fenfluramine was administered at a dose of 0.5 to 1 mg/kg/day, this resulted in a reduction in the number of seizures experienced by the patients, and concluded that "this drug could have significant anti-epileptic activity in a selected group of young patients with idiopathy or symptomatic generalized epilepsy, namely, children with self-induced seizures." The authors noted that "[i]t may well be that fenfluramine has no direct antiepileptic activity but acts through its effect on the compulsion to induce seizures." Hence, the authors suggested that fenfluramine affected behavior and not the seizure itself.

In a letter to *Epilepsia*, published in that journal (*Epilepsia*, 43(2):205-206, 2002), Boel and Casaer commented that fenfluramine appeared to be of therapeutic benefit in patients with intractable epilepsy and self-induced seizures. However, the authors did not attribute fenfluramine's efficacy to generalized anti-seizure activity.

Another form of epilepsy that may be treated with fenfluramine is Lennox-Gastaut syndrome (LGS). LGS was first described in 1960, and named for neurologists William G. Lennox (Boston, USA) and Henri Gastaut (Marseille, France). It is a difficult-to-treat form of childhood-onset epilepsy that most often appears between the second and sixth year of life, although it can occur at an earlier or later age. LGS is characterized by frequent seizures and different seizure types; it is typically accompanied by developmental delay and psychological and behavioral problems. In children, common causes of LGS include perinatal brain injury, brain malformations such as tuberous sclerosis or cortical dysplasia, CNS infection, and degenerative or metabolic disorders of the nervous system.

Daily multiple seizures of different types are typical in LGS. Also typical is the broad range of seizures that can occur. The most common seizure types are tonic-axial, atonic, and absence seizures, but myoclonic, generalized tonic-clonic, and focal seizures can also occur in any LGS patient. Atonic, atypical absence, tonic, focal, and tonic-clonic seizures are also common. Additionally, many LGS patients will have status epilepticus, often of the nonconvulsive type, which is characterized by dizziness, apathy, and unresponsiveness. Further, most patients have atonic seizures, also called drop seizures, which cause their muscles to go limp and result in the patient suddenly and unexpectedly to fall to the ground, often causing significant injury, which is why patients often wear a helmet to prevent head injury.

In addition to daily multiple seizures of various types, children with LGS frequently have arrested/slowed psychomotor development and behavior disorders. The syndrome is also characterized by a specific finding on electroencephalogram (EEG), specifically interictal (i.e., between-seizures) slow spike-wave complexes and fast activity during sleep.

The optimum treatment for LGS has yet to be established. A variety of therapeutic approaches are currently used in LGS, including conventional antiepileptic medications, diet and surgery, however the evidence supporting these therapies is not robust and treatment remains most often ineffective. The use of several common first-line treatments is based on clinical experience or conventional wisdom; examples include broad spectrum anti-convulsant medications, such as valproic acid, and benzodiazepines, most often clonazepam and clobazam. A few drugs have been proven effective for some patients for certain seizure types by double-blind placebo-controlled studies; examples include clobazam, lamotrigine, topiramate, felbamate, and rufinamide, although most patients continue to have significant seizures even while taking these medications. Second-line medications currently in use, such as zonisamide, are prescribed based on results of some open-label uncontrolled studies. The ketogenic diet may be useful in some patients with LGS refractory to medical treatment. Surgical options for LGS include corpus callostomy (for drop attacks), vagus nerve stimulation, and focal cortical resection (in the presence of a single resectable lesion). However, it should be noted that significant improvement from any of these therapies alone or in combination is a rare occurrence.

Despite the severity of LGS's symptoms and the frequency with which it occurs (it accounts for up to 10% of all childhood epilepsies), there is currently no standard evidence-based treatment for the disease. A comprehensive review of the literature [see Hancock E C & Cross J H, Treatment of Lennox-Gastaut syndrome (Review), published in *The Cochrane* Library 2013, Issue 2] discovered only nine randomized controlled trials which evaluated the pharmaceutical treatment of the syndrome. The authors concluded that there is a paucity of research and " . . . that no monotherapy (to date) has been shown to be highly effective in this syndrome." Id at page 12. The authors further concluded that "[t]he optimum treatment for LGS remains uncertain and no study to date has shown any one drug to be highly efficacious". Id at page 12.

Fenfluramine shows promise in the treatment of certain epilepsies and/or epileptic encephalopathies. See Lagae et al., "Add-on Therapy with Low Dose Fenfluramine (ZX008) in Lennox Gastaut Syndrome" Abstract 3.366, 2016, presented at the AES 2016 Annual Meeting in Houston, Tx (presenting the results of a single center Phase 2 pilot open label dose finding trial of fenfluramine as an add-on therapy; text and figures available at: https://www.aesnet.org/meetings_events/annual_meeting_abstracts/view/240065); see also U.S. patent application Ser. No. 15/246,346.

Thus, there is a dire, long felt, but previously unmet need for therapeutic agents effective in treating, preventing or ameliorating the frequent severe seizures suffered by patients with refractory epilepsy syndromes. The present disclosure has applicability with respect to a range of different types of epilepsies and epilepsy subtypes, including Dravet syndrome, Doose syndrome, infantile spasms, West syndrome and Lennox-Gastaut syndrome.

BRIEF SUMMARY

The methods disclosed herein are generally useful for treating, preventing or ameliorating symptoms associated with seizure disorders in a patient in need of such treatment. For example, the disclosed methods are useful in preventing, treating or ameliorating symptoms associated with refractory seizure disorders for which conventional antiepileptic drugs are inadequate, ineffective, or contraindicated, including but not limited to Dravet syndrome, Lennox-Gastaut syndrome, Doose syndrome, infantile spasms, West syndrome.

In some aspects, provided herein is a method of reducing frequency or severity of seizures or Sudden Unexpected Death in Epilepsy (SUDEP) in a human patient, comprising administering to the patient a therapeutically effective dose of a 5-hydroxytryptamine receptor 4 agonist (5-HT$_4$ agonist), and allowing the 5-HT$_4$ agonist to stimulate 5-HT$_4$ receptors in the patient, thereby reducing the incidence, frequency or severity of seizures in the patient.

In some aspects, provided herein is a method of inhibiting seizure-induced respiratory arrest (S-IRA) in a human patient, comprising administering to the patient a therapeutically effective dose of a 5-HT$_4$ agonist, and allowing the 5-HT$_4$ agonist to stimulate 5-HT$_4$ receptors in the patient, thereby inhibiting S-IRA in the patient.

In some aspects, provided herein is a method of reducing the length of the mean post-ictal depression (PID) period in a human patient, comprising administering to the patient a therapeutically effective dose of a 5-HT$_4$ agonist, and allowing the 5-HT$_4$ agonist to stimulate 5-HT$_4$ receptors in the patient, thereby inhibiting PID period in the patient.

In some aspects, provided herein is a method of reducing likelihood of seizure-induced Sudden Unexpected Death in Epilepsy (SUDEP) in a human patient, comprising administering to the patient a therapeutically effective dose of a 5-HT$_4$ agonist, and allowing the 5-HT$_4$ agonist to stimulate 5-HT$_4$ receptors in the patient, thereby reducing the likelihood of SUDEP in the patient.

In some aspects, provided herein is a method of stimulating one or more 5-HT$_4$ receptors in the brain of a patient diagnosed with a possibility of seizure-induced sudden death in epilepsy (SUDEP) wherein the patient exhibits seizures, comprising administering an effective dose of a 5-HT$_4$ agonist to the patient, and allowing the 5-HT$_4$ agonist to stimulate 5-HT$_4$ receptors in the patient and thereby reduce a possibility of SUDEP in the patient.

In some embodiments of the method, the 5-HT$_4$ agonist is selected from the group consisting of fenfluramine, BIMU-8, Cisapride, Mosapride, Prucalopride, Renzapride, RS-67506, Tegaserod, Zacopride, Metoclopramide, and Sulpiride or a pharmaceutically acceptable salt thereof.

In some embodiments of the method, the 5-HT$_4$ agonist is fenfluramine, or a pharmaceutically acceptable salt thereof.

In some embodiments, the fenfluramine is administered as an adjunctive therapeutic agent.

In some embodiments, the therapeutically effective dose of fenfluramine is selected from the group consisting of 0.2 mg/kg/day to 0.08 mg/kg/day up to a 30 mg maximum daily dose.

In some embodiments of the method, the therapeutically effective dose of fenfluramine is 0.8 mg/kg/day to 0.01 mg/kg/day.

In some embodiments of the method, the therapeutically effective dose of fenfluramine is administered in a dosage form selected from the groups consisting of oral, injectable, transdermal, inhaled, nasal, rectal, vaginal and parenteral.

In some embodiments of the method, the therapeutically effective dose of fenfluramine is administered in an oral liquid dosage form.

In some embodiments, the method further comprises administering to the patient an effective dose of stiripentol or a pharmaceutically acceptable salt thereof.

In some embodiments, the method further comprises administering to the patient an effective dose of valproate or a pharmaceutically acceptable salt thereof.

In some embodiments, the method further comprises administering to the patient an effective dose of clobazam or a pharmaceutically acceptable salt thereof.

In some embodiments of the method, an effective dose is less than 10.0 mg/kg/day, or less than 1.0 mg/kg/day, or approximately 0.8 mg/kg/day, or approximately 0.5 mg/kg/day, or approximately 0.2 mg/kg/day, or approximately 0.1 mg/kg/day; or approximately 0.01 mg/kg/day. In some embodiments of the method, the effective dose of fenfluramine is 0.5 mg/kg/day. In some embodiments of the method, the effective dose of fenfluramine is between 0.01 mg/kg/day and 0.8 mg/kg/day.

In some embodiments, the dosage form is an oral composition in an amount selected from the group consisting of 30 mg/day or less, 20 mg/day or less, 10 mg/day or less and 5 mg/day or less.

In some embodiments of the method, the fenfluramine is formulated with a pharmaceutically acceptable carrier.

In some embodiments of the method, the fenfluramine is the sole (only) pharmaceutically active drug administered to the patient.

In some embodiments of the method, the 5-HT$_4$ agonist is at least one of:
 (a) inactive at the 5-HT$_{2B}$ receptor;
 (b) a neutral agonist of the 5-HT$_{2B}$ receptor; and
 (c) an inverse agonist of the 5-HT$_{2B}$ receptor 5-HT$_{2B}$ receptor.

In some embodiments, the patient exhibits a significantly higher responder rates compared with placebo.

In some embodiments, the method further includes repeating the administering over a period of days until the patient exhibits a 40% reduction from baseline in convulsive seizure frequency.

In some embodiments, the patient exhibits at least a ≥50% reduction in the frequency of convulsive seizures.

In some embodiments, the patient exhibits at least a ≥75% reduction in the frequency of convulsive seizures.

In some embodiments, the patient exhibits at least a ≥90% reduction in the frequency of convulsive seizures.

In some embodiments, the patient completely free of seizures.

In some embodiments, the patient is alive after two years after first administration of the 5-HT$_4$ agonist.

In some embodiments, the method further includes repeating the administering until the patient is seizure free for a period of ≥1 day.

In some embodiments, the method further includes repeating the administering until the patient is seizure free for a period of ≥1 week.

In some embodiments, the method further includes repeating the administering until the patient is seizure free for a period of ≥1 month.

In some embodiments, the method further includes repeating the administering until the patient is seizure free for a period of ≥1 year.

In some embodiments, the method further includes repeating the administering until the patient is permanently seizure free.

In some embodiments of the method, the subject/patient has been diagnosed with an epilepsy syndrome selected from the group consisting of Dravet syndrome, Lennox-Gastaut syndrome, Doose syndrome, infantile spasms, West syndrome, and refractory epilepsy. In some embodiments, the subject/patient may also be, have been, or is being treated for epilepsy. In some embodiments, the subject/patient is being treated for epilepsy or epileptic encephalopathy, e.g., Dravet syndrome and/or Lennox-Gastaut syndrome. In some embodiments, the subject/patient is 18 years of age or younger. In other embodiments, the subject/patient is an adult (18 years of age or older).

In some embodiments of the present disclosure, a symptom of the epileptic encephalopathy is seizure (e.g., convulsive seizures or non-convulsive seizures). In some embodiments of the present disclosure, a symptom of the epileptic encephalopathy is seizure-induced Sudden Unexpected Death in Epilepsy (SUDEP). In some embodiments of the present disclosure, a symptom of the epileptic encephalopathy is post-ictal depression (PID). In some embodiments of the present disclosure, a symptom of the epileptic encephalopathy is seizure-induced respiratory arrest (S-IRA).

In some embodiments of the method, an effective dose of the 5-HT4 agonist is administered in a pharmaceutically acceptable carrier.

In some embodiments of the method, the 5-$HT_4$ agonist is in a formulation adapted to a dosage forms selected from the group consisting of an oral dosage form, an intravenous dosage form, rectal dosage form, subcutaneous dosage form, and a transdermal dosage form.

In some embodiments of the method, the oral dosage form is selected from the group consisting of a liquid, a suspension, a tablet, a capsule, a lozenge, and a dissolving strip.

In another aspect, the disclosure provides a kit comprising a therapeutic agent, e.g., a 5-$HT_4$ agonist, as used in any of the methods disclosed herein, and instructions for use.

As shown above and as will be recognized by others skilled in the art, the therapeutic agents provide the important advantage that they are more effective and/or exhibit an improved safety profile as compared to fenfluramine or to other therapeutic agents and methods currently known in the art.

These and other objects, advantages, and features of the invention will become apparent to those persons skilled in the art upon reading the details of the therapeutic agents and methods of using the same as are more fully described below.

BRIEF DESCRIPTION OF THE DRAWINGS

The invention is best understood from the following detailed description when read in conjunction with the accompanying drawings. Included in the drawings are the following figures:

FIGS. 1A-1D: show the dose- and time-dependent anticonvulsant effects of fenfluramine (FFA) on susceptibility of DBA/1 mice to audiogenic seizures (AGSz).

FIGS. 4A and 4B: show the reduction in incidence (frequency) of severe seizures and prevention of S-IRA by FFA pretreatment.

FIG. 8: illustrates that the 5-$HT_4$ antagonist (GR125487) partially reverses S-IRA blocking effect of fenfluramine.

DETAILED DESCRIPTION

Figure 1A:
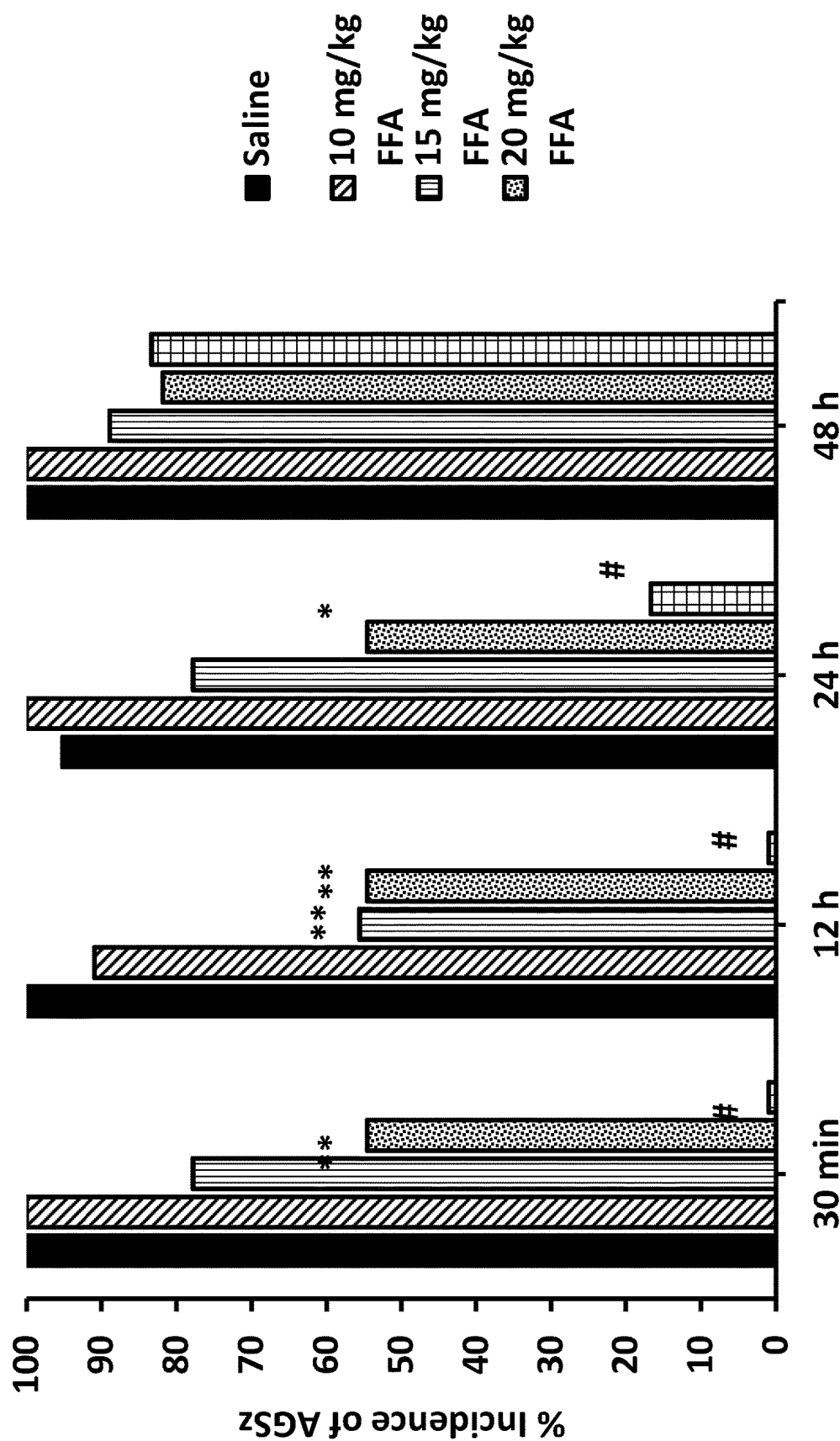

Before the present compositions and methods are described, it is to be understood that this invention is not limited to the particular formulations and methods described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those include limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims the singular forms "a," "an," and "the" include plural referents unless the context clearly dictates otherwise.

Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing of the present application. Nothing herein is to be construed as an admission that the present invention is not entitled to antedate such publication by virtue of prior invention. Further, the dates of publication provided may be different from the actual publication dates which may need to be independently confirmed.

The invention here is based on the surprising discovery that agonists of the 5-HT$_4$ receptor reduce the likelihood and/or occurrence of Sudden Unexpected Death in Epilepsy (SUDEP) or the severity of seizures in a human patient exhibiting, experiencing, and/or diagnosed with epilepsy or epileptic encephalopathy.

Thus, the disclosure provides methods which employ certain therapeutic agents useful in treating patients diagnosed with a seizure disease or disorder who require treatment. The disclosure further provides methods which employ certain therapeutic agents useful in preventing, treating or ameliorating symptoms associated with seizure diseases or disorders in patients who require treatment.

The methods disclosed herein comprise administering a therapeutically effective amount of one or more therapeutic agents. A number of therapeutic agents can be employed in the methods of the present invention. In some embodiments, the therapeutic agent is a 5-HT$_4$ receptor agonist. In some embodiments, the therapeutic agent is active at one or more targets, or two or more targets, or three or more targets, or four or more targets, or five or more targets, or more. In some embodiments, the therapeutic agent is active at the 5-HT$_4$ receptor.

The present disclosure provides a method of preventing, treating or ameliorating symptoms associated with seizure diseases or disorders in patient who requires treatment, wherein the therapeutic agent is a compound that is active at one or more targets. In some aspects, the therapeutic agent comprises a compound that activates a 5-HT receptor protein such as an agonist of the 5-HT$_4$ receptor.

The disclosure further provides pharmaceutical compositions comprising one or more of the therapeutic agents disclosed herein for use in the methods of the invention. In some embodiments, the pharmaceutical compositions are formulations adapted to one or more dosage forms comprising an oral dosage form, an intravenous dosage form, rectal dosage form, subcutaneous dosage form, and a transdermal dosage form. In particular embodiments, the oral dosage forms are selected from the group consisting of a liquid, a suspension, a tablet, a capsule, a lozenge, and a dissolving strip. In one embodiment, the transdermal dosage form is a patch.

The disclosure further provides methods of preventing, treating or ameliorating one or more symptoms of a disease or disorder in a patient diagnosed with that disease or disorder. In one embodiment of this aspect, the patient has been diagnosed with a seizure disorder. In further embodiments, the seizure disorder is a form of intractable epilepsy, such as Dravet syndrome, Lennox-Gastaut syndrome, Doose syndrome, and West syndrome, and other forms of refractory epilepsy. In another embodiment, the symptom is a seizure, more particularly status epilepticus. In another embodiment, the disclosure provides methods of preventing, or reducing the incidence (frequency) of Sudden Unexpected Death in Epilepsy (SUDEP) in a population of patients. In another embodiment, the patient is obese.

Epilepsy is associated with a two to three-fold increase in premature mortality compared to the general population. A major cause for this premature mortality increase is Sudden Unexpected Death in Epilepsy (SUDEP), which occurs under benign circumstances associated with terminal seizures but excludes drowning, trauma, toxicological effect, or status epilepticus-related deaths. Most of the witnessed clinical cases of SUDEP reported generalized seizures leading to respiratory and cardiac failure. The lifetime risk of SUDEP among epileptics is estimated to be up to 8%, and young persons with epilepsy are at a 24 or 28-fold higher risk of sudden unexpected death than the general population. SUDEP ranks second only to stroke among neurologic diseases, in terms of potential years of life lost. The major pathophysiological mechanisms that have been implicated in SUDEP include respiratory failure, cardiac arrhythmia and cerebral shutdown. Because no effective treatments are currently available, there is a pressing need to find drugs that could prevent SUDEP. One measure of severity of seizures is to count the frequency and/or duration.

The DBA/1 mouse model of SUDEP exhibits a chronic, abnormally high degree of susceptibility to fatal seizures (seizure-induced death) induced by electroconvulsive shock, hyperthermia, convulsant drug, and acoustic stimulation. High intensity acoustic stimuli induce audiogenic seizures (AGSz), which consist of tonic-clonic seizures followed by seizure-induced respiratory arrest (S-IRA) that leads to death in the immediate post-ictal period. Timely mechanical support of respiration can consistently reverse S-IRA in this SUDEP model. (Faingold C L, Randall M, Tupal S. 2010. DBA/1 mice exhibit chronic susceptibility to audiogenic seizures followed by sudden death associated with respiratory arrest. *Epilepsy Behav.* 17:436-40).

Studies have elucidated deficits in serotonin production and receptor expression in DBA/1 mice. Many, but not all drugs that enhance serotonergic neurotransmission, including selective serotonin reuptake inhibitors (SSRIs), such as fluoxetine, fluvoxamine and sertraline, or inhibit serotonin-norepinephrine reuptake, such as venlafaxine and atomoxetine, have been reported to prevent seizure-induced respiratory failure and death in DBA mice in a dose-dependent manner. In contrast, serotonin antagonists enhance the susceptibility of DBA mice to S-IRA. These findings and additional studies on other SUDEP models have led to a serotonergic hypothesis of SUDEP.

The serotonin hypothesis of SUDEP is based on findings that treatments which modify serotonergic function significantly alter susceptibility to seizure-induced sudden death in several epilepsy models, including DBA/1 mice. Serotonergic abnormalities have also recently been observed in human SUDEP.

As disclosed in US Patent Application publication 2018/0092864 (U.S. Ser. No. 15/717,159), the contents of which are incorporated herein by reference in their entirety, methods are provided for determining the binding characteristics, activity (e.g., agonist or antagonist) selectivity, specificity and pharmaceutical effects of fenfluramine and fenfluramine analogs at various receptors, including (5-HT) receptor sub-types, (e.g., 5-HT$_{1A}$, 5-HT$_1$, 5-HT$_{1E}$, 5-HT$_{2A}$, 5-HT$_{2C}$, 5-HT$_4$, 5-HT$_{5A}$ and 5-HT$_7$) as well as other receptors, such as, for example, an adrenergic receptor (e.g., the beta-1 or beta-2 adrenergic receptors), a muscarinic acetylcholine receptor protein (e.g., the M1, M2, M3, M4 or M5 muscarinic acetylcholine receptor), a chaperone protein (e.g., the Sigma 1 or Sigma-2 receptors), or a voltage-gated sodium channel subunit protein or a subunit thereof (e.g., the Nav 1.1, Nav 1.2, Nav 1.3, Nav 1.4, Nav 1.5, Nav 1.6, or Nav 1.7) and/or a neurotransmitter transport protein (e.g., a serotonin transporter (SET), a dopamine transporter (DAT), and a norepinephrine transporter (NET)). Testing in animal models led to the unexpected discovery that certain of those candidates surprisingly reduced epileptiform activity in in vivo animal models.

Recently, the contributions of several serotonin receptor subtype(s) in mediating the action of fenfluramine in blocking seizure-induced sudden death were evaluated in the DBA/1 mouse model of SUDEP. In these studies, fenfluramine, known to enhance the release of serotonin (5-hydroxytryptamine, 5-HT) in the brain, was found to be effective in blocking audiogenic seizures (AGSz) and seizure-induced respiratory arrest (S-IRA) in DBA/1 mice. However, before the present disclosure, it was unknown whether fenfluramine's effect was mediated by specific 5-HT receptors. Thus, as is presently disclosed, several 5-HT receptor-specific antagonists were used to investigate fenfluramine's effects, to determine whether the 5-HT antagonists could reverse the anticonvulsant activity (and/or S-IRA blocking, or any other effect) mediated by fenfluramine, and identify a subset of 5-HT receptors to which fenfluramine binds and acts as an agonist.

For these experiments, DBA/1 mice (N=287) were used (after subjecting to the established priming procedure to assure consistent susceptibility to S-IRA following AGSz) to assess the effects of fenfluramine on various 5-HT receptors. Seizures were induced using an electrical bell, and resuscitation was accomplished using a rodent respirator (Faingold et al., 2010). At least 24 hours after priming, the mice received FFA (15 mg/kg, i.p.) and were tested for AGSz and S-IRA susceptibility 16 hours later. Thirty minutes prior to AGSz induction, a selective 5-HT receptor antagonist or vehicle was administered to evaluate if a specific receptor contributes to the ability of FFA to block S-IRA. Seizure behaviors were recorded on videotape, quantified, and compared statistically with vehicle-treated negative and FFA-treated positive controls (Chi-Square Test; significance set at p<0.05).

Specifically, the antagonists tested were: the 5-HT$_{1A}$ antagonist WAY100635 (0.1-15 mg/kg); the 5-HT$_2$ antagonist Ritanserin (10-20 mg/kg); the 5-HT$_3$ antagonist Ondansetron (1-3 mg/kg); the 5-HT$_4$ antagonist GR125487 (20-60 mg/kg); the 5-HT$_{5A}$ antagonist SB669551 (10-20 mg/kg); and the 5-HT$_7$ antagonist SB269970 (30-40 mg/kg). Studies investigating the effect of 5-HT$_6$ and 5-HT$_{1a/1b}$ antagonists are also underway.

Notably, a reversal of the FFA-induced reduction in the incidence (frequency) of S-IRA was observed following treatment with the 5-HT4 antagonist (GR125487, 30 mg/kg). This dose was effective in inducing a significant (p<0.05) blockade of this of the FFA-induced reduction in S-IRA. While the antagonists of 5-HT$_2$, 5-HT$_4$ and 5-HT$_7$ receptors were found to reverse the anticonvulsant effect of FFA against the severity of AGSz in the mice, but not FFA's S-IRA blocking effect, 5-HT$_{1a}$ and 5-HT$_3$ receptor antagonists were not effective at any dose tested.

Figure 7:
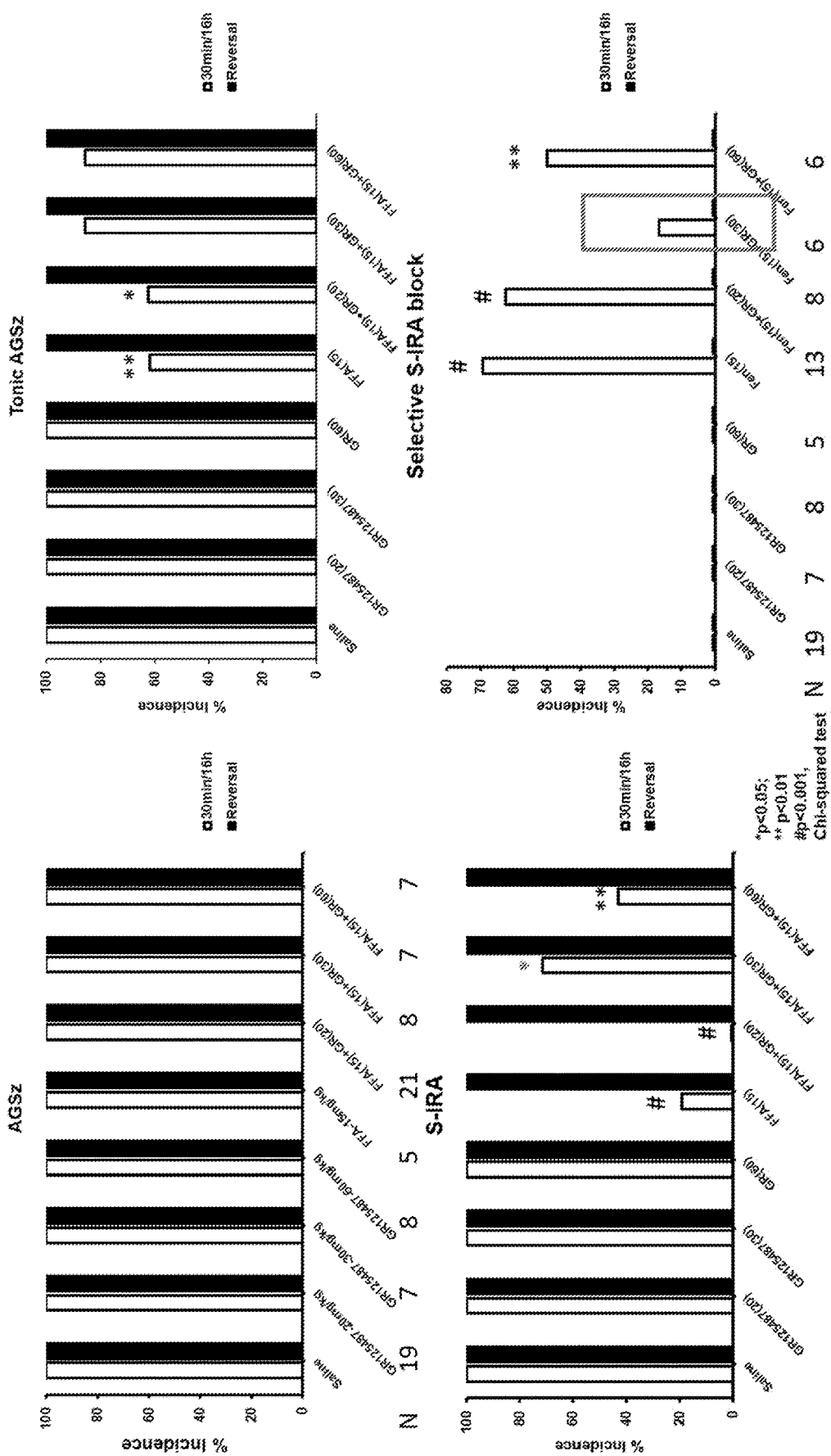
FIG. 7: shows the effect of the 5-$HT_4$ antagonist (GR125487) on S-IRA blocking by FFA.

Specifically, a significant (p<0.05) partial reversal of the FFA-induced S-IRA blockade was observed following 30-minutes treatment with the 5-HT$_4$ antagonist (GR125487, 30 mg/kg). Thus, GR125487 was effective in inducing a significant blockade of fenfluramine's inhibition of S-IRA (See FIGS. 7 and 8). Interestingly, antagonists of 5-HT$_2$, 5-HT$_4$ and 5-HT$_7$ receptors were found to reverse the anticonvulsant effect of FFA against the severity of AGSz but not its S-IRA blocking effect.

The antagonists of 5-HT$_2$ (20 mg/kg Ritanserin), 5-HT$_4$ (30 and 60 mg/kg GR125487) and 5-HT$_7$ (30 mg/kg and 40 mg/kg SB269970) receptors were able to reverse FFA's anticonvulsant effect against the severity of AGSz. The 5-HT$_{5a}$ antagonist SB669551 blocked FFA's anticonvulsant effect at 20 mg/kg. In contrast, 5-HT$_{1A}$ (WAY100635 at 0.1-15 mg/kg) and 5-HT$_3$ (Ondansetron at 1-3 mg/kg) receptor antagonists were not effective at any dose tested.

These findings suggest that the anticonvulsant effect of FFA against S-IRA induced by AGSz in DBA/1 mice is mediated, relatively selectively, as a result of activation of 5-HT$_4$ receptors. It may be relevant that the expression levels of 5-HT$_4$ receptors in the DBA/1 mouse brain is not significantly different from that in normal mice (Faingold et al., 2011). The results were surprising in light of previous studies on the receptors that mediate the ability of a selective serotonin re-uptake inhibitor to reduce seizure severity and block S-IRA can be reversed only by a selective 5-HT$_3$ antagonist (Faingold et al., 2016). Thus, agonists which activate specific 5-HT receptors (e.g., 5-HT$_4$ receptor agonists) are of interest for future studies in animal models of SUDEP and as a potential preventative treatment for human SUDEP.

Generally, antagonists of the 5-HR$_{1A}$, 5-HT$_3$, and receptors did not reverse fenfluramine's effect, suggesting that fenfluramine's effect on S-IRA and/or AGSz is not mediated by an interaction with these receptors. In contrast, the 5-HT$_2$, 5-HT$_{5A}$, 5-HT$_7$ antagonists (Ritanserin at 20 mg/kg; SB669551 at 20 mg/kg; and SB269970 at 30 mg/kg and 40 mg/kg) were found to block FFA's anticonvulsant effect, suggesting that fenfluramine's anticonvulsant effect may be mediated by its interaction of these receptors. Notably, because the compound GR125487 was found to partially reverse fenfluramine's anticonvulsant effects and S-IRA blocking effects, it was concluded that fenfluramine was found to act specifically as an agonist at the 5-HT$_4$ receptor.

Thus, the anticonvulsant effect of FFA against S-IRA induced by AGSz in DBA/1 mice is mediated, at least in part, by activation of 5-HT$_4$ receptors. The expression level of 5-HT$_4$ receptors in the DBA/1 mouse brain is not significantly different from that in normal mice (Faingold et al., 2011). These results were surprising in light of previous studies on the receptors that mediate the ability of a selective serotonin re-uptake inhibitor to reduce seizure severity and block S-IRA can be reversed only by a selective 5-HT$_3$ antagonist (Faingold et al., 2016).

Agonists which activate specific 5-HT receptors are of interest for future studies in animal models of SUDEP and as a potential preventative treatment for human SUDEP.

The present disclosure is directed to methods of reducing incidence (frequency) or severity of seizures in a human patient, comprising administering to the patient a therapeutically effective dose of a 5-HT$_4$ agonist, and allowing the 5-HT$_4$ agonist to stimulate 5-HT$_4$ receptors in the patient, thereby reducing the incidence (frequency) or severity of seizures in the patient, wherein the 5-HT$_4$ agonist is fenfluramine.

The present disclosure is directed to methods of inhibiting seizure-induced respiratory arrest (S-IRA) in a human patient, comprising administering to the patient a therapeutically effective dose of a 5-HT$_4$ agonist, and allowing the 5-HT$_4$ agonist to stimulate 5-HT$_4$ receptors in the patient, thereby inhibiting seizure-induced respiratory arrest (S-IRA) in the patient, wherein the 5-HT$_4$ agonist is fenfluramine.

The present disclosure is directed to methods of reducing the length of the mean post-ictal depression (PID) period in a human patient, comprising administering to the patient a therapeutically effective dose of a 5-HT$_4$ agonist, and allowing the 5-HT$_4$ agonist to stimulate 5-HT$_4$ receptors in the patient, thereby reducing the length of the mean post-ictal depression (PID) period after seizure in the patient, wherein the 5-HT$_4$ agonist is fenfluramine.

The present disclosure is directed to methods of reducing likelihood of seizure-induced Sudden Unexpected Death in Epilepsy (SUDEP) in a human patient, comprising administering to the patient a therapeutically effective dose of a 5-HT$_4$ agonist, and allowing the 5-HT$_4$ agonist to stimulate 5-HT$_4$ receptors in the patient, thereby reducing likelihood of SUDEP in the patient, wherein the 5-HT$_4$ agonist is fenfluramine.

Thus, one method proposed for treating epilepsy and/or epileptic encephalopathy is to stimulate one or more 5-HT receptors in the brain of a patient may be to administer an effective dose of fenfluramine to said patient. In some embodiments of this disclosure, the one or more 5-HT receptors are selected from 5-HT$_1$, 5-HT$_{1A}$, 5-HT$_{1B}$, 5-HT$_{1C}$, 5-HT$_{1D}$, 5-HT$_{1E}$, 5-HT$_{1F}$, 5-HT$_2$, 5-HT$_{2A}$, 5-HT$_{2B}$, 5-HT$_{2C}$, 5-HT$_3$, 5-HT$_4$, 5-HT$_5$, 5-HT$_{5A}$, 5-HT$_{5B}$ 5-HT$_6$, and 5-HT$_7$ amongst others. In some embodiments of this disclosure, the 5-HT receptor is 5-HT$_4$. In certain embodiments of this disclosure, the patient has been diagnosed with epilepsy.

Without being bound by theory, Fenfluramine (FFA) enhances serotonergic neurotransmission by augmenting carrier-mediated synaptic release of serotonin (5-HT) in the brain due to disruption of its vesicular storage and inhibiting its reuptake. Its active metabolite, norfenfluramine (N-FFA), contributes to prolonging this effect. Recent clinical studies found treatment with FFA to be effective as an add-on (adjunctive) agent to improve seizure control in patients with the intractable seizures characteristic of Dravet syndrome, which is difficult to treat and has a tragically high risk of SUDEP. Seizure activity was significantly reduced in frequency and/or severity, and in some cases eliminated entirely, by administering the drug fenfluramine.

Studies in the zebrafish model of Dravet syndrome also found FFA to be effective in blocking electrographic as well as seizure-like behavioral activity. In light of these findings, the present disclosure examined whether fenfluramine can decrease S-IRA susceptibility and reduce seizure frequency and/or severity in DBA/1 mice.

The present disclosure is the first study to investigate the efficacy of FFA in a mammalian model of SUDEP. Thus, the present disclosure is directed to elucidating the effects of FFA on seizures; additionally, the effect of FFA on seizure-induced respiratory arrest (S-IRA) in DBA/1 mice was investigated.

As disclosed herein, fenfluramine was found to act as an anticonvulsant at a particular serotonin receptor subtype to prevent seizure-induced respiratory arrest (S-IRA) and seizure-induced Sudden Unexpected Death in Epilepsy (SUDEP) in the DBA/1 mouse model. Until the present disclosure, the mechanism for efficacy of FFA in the treatment of seizures was not known, and it was unclear whether the effect of FFA was mediated by any specific 5-HT receptors. The present study found that FFA has a specific effect at a particular 5-HT receptor subtype, and further determined that specific 5-HT antagonists could reverse the anticonvulsant effects and S-IRA blocking effects of FFA. In some embodiments of this disclosure, the 5-HT receptor is 5-HT$_4$.

Fenfluramine (FFA), which acts to enhance the release of serotonin (5-hydroxytryptamine, 5-HT) in the brain, was found to be effective in blocking audiogenic seizures (AGSz) and seizure-induced respiratory arrest in these DBA/1 mice.

Specific Aspects of the Invention

Provided are therapeutic agents that are useful in preventing, treating, or ameliorating symptoms associated with a disease or disorder in a patient diagnosed with the disease or disorder, including but not limited to patients diagnosed with refractory epilepsy or epileptic encephalopathy, including but not limited to Dravet syndrome, Lennox-Gastaut syndrome, Doose syndrome, infantile spasms and West syndrome, and other refractory epilepsies. Also provided are methods of preventing, treating or ameliorating symptoms such as seizures and seizure-induced respiratory arrest (S-IRA) leading to Sudden Unexpected Death in Epilepsy (SUDEP) associated with a disease or disorder in a patient diagnosed with that disease or disorder, and pharmaceutical compositions and formulations comprising those agents that are useful in practicing the methods of the invention.

Therapeutic Agents

The inventors have made the surprising discovery that certain therapeutic agents (e.g. fenfluramine (FFA)) are useful in treating diseases or disorders, including but not limited to diseases or disorders associated with epilepsy or epileptic encephalopathy, and exhibiting intractable seizures, seizure-induced respiratory arrest (S-IRA) and/or Sudden Unexpected Death in Epilepsy (SUDEP). Thus, in accordance with one aspect of the present disclosure, provided herein are therapeutic agents useful in treating patients diagnosed with a disease or disorder and/or in preventing or ameliorating symptoms of those diseases or disorders exhibited by the patient.

Dosage/Frequency of Administration: Dosage forms can be formulated for once a day administration, or for multiple daily administrations (e.g. 2, 3 or 4 times a day administration). Alternatively, for convenience, dosage forms can be formulated for less frequent administration (e.g., monthly, bi-weekly, weekly, every fourth day, every third day, or every second day), and formulations which facilitate extended release are known in the art.

As used herein, the phrase "semi-chronic administration" refers to administration of a therapeutic agent, such as fenfluramine or a 5-HT$_4$ receptor agonist, for a period of several days, a week, several weeks, a month, several months, a year, or several years.

Binding of Single or Multiple Targets

In some embodiments, the therapeutic agents provided by the disclosure can bind one or more targets, for example, two or more targets, three or more targets, four or more targets, five or more targets, or more.

Receptor Protein Targets

In some embodiments, the therapeutic agent binds a 5-HT$_4$ receptor.

In some embodiments, the therapeutic agent binds to the sigma-1 receptor and one or more 5-HT receptors, for example, the 5-HT$_{1A}$ receptor, the 5-HT$_{1D}$ receptor, the 5-HT$_{1E}$ receptor, the 5-HT$_{2A}$ receptor, the 5-HT$_{2C}$ receptor, the 5-HT$_4$ receptor, the 5-HT$_{5A}$ receptor, and/or the 5-HT$_7$ receptor. In some embodiments, the therapeutic agent binds to the sigma-1 receptor and the 5-HT$_4$ receptor.

Functional Activity

In accordance with the present disclosure, the terms "active" or "activity" are used herein to mean having an effect on cell, nuclear, or tissue function, and is intended to encompass agonist activity, inverse agonist activity, antagonist activity, synergy, allosteric agonism, allosteric modulation, including positive, negative and neutral allosteric modulation, ago-allosteric modulation, including positive, negative, and neutral ago-allosteric modulation, and ligand trapping.

Receptor Activity

In some embodiments, the therapeutic agent is active at one or more 5-HT receptor proteins selected from the group consisting of the 5-HT$_{1A}$ receptor, the 5-HT$_{1D}$ receptor, the 5-HT$_{1E}$ receptor, the 5-HT$_{2A}$ receptor, the 5-HT$_{2C}$ receptor, the 5-HT$_4$ receptor, the 5-HT$_{5A}$ receptor, and/or the 5-HT$_7$ receptor. In some embodiments, the therapeutic agent is active at the 5-HT$_4$ receptor.

Therapeutic Agents Active at Multiple Targets

The disclosure further provides therapeutic agents that are active one or more targets, for example, two or more targets, three or more targets, four or more targets, five or more targets, or more.

For example, in one embodiment, the disclosure provides therapeutic agents that are active at two or more 5-HT receptors. In this regard, the present disclosure is directed to the surprising discovery that fenfluramine acts on the 5-HT$_4$ receptors and is useful in preventing, treating or ameliorating symptoms such as seizure-induced respiratory arrest (S-IRA) leading to Sudden Unexpected Death in Epilepsy (SUDEP) in patients having a seizure disease or disorder, epilepsy and/or epileptic encephalopathy.

Therapeutic Agents which are Inactive at the 5-HT$_{2B}$ Receptor

In preferred embodiments, the therapeutic agents disclosed herein are not active at the 5-HT$_{2B}$ receptor to an extent sufficient to cause adverse effects such as valvulopathy, pulmonary hypertension or other adverse effects. In alternate exemplary embodiments, the agents do not bind the 5-HT$_{2B}$ receptor, or are 5-HT$_{2B}$ antagonists (i.e., agents that block the activity of agonists), or are 5-HT$_{2B}$ inverse antagonists (i.e., agents that decrease basal activity of the receptor), or are neutral agonists (i.e., compounds that block binding of agonists) of the 5-HT$_{2B}$ receptor.

Diseases and Disorders

The therapeutic agents provided by the disclosure are useful in treating a number of diseases and disorders, and/or in reducing or ameliorating their symptoms. For example, the therapeutic agents disclosed herein are useful for treating forms of epilepsy such as Dravet syndrome, Lennox-Gastaut syndrome, Doose syndrome, infantile spasms, West syndrome, and other refractory epilepsy syndromes, and in preventing, reducing or ameliorating their symptoms in patients diagnosed with those conditions. The therapeutic agents provided herein are also useful in preventing cognition disorders that affects learning, memory, perception, and/or problem solving, including but not limited to amnesia, dementia, and delirium.

Methods of Use

The above-described therapeutic agents can be employed in a variety of methods. As summarized above, aspects of the method include administering a therapeutically effective amount of a therapeutic agent as described herein to treat a patient in need of treatment, for example, to a patient diagnosed with a disease or condition of interest, or to prevent, reduce or ameliorate symptoms of a disease or disorder in patients diagnosed with that disease or disorder. Examples include seizures, particularly status epilepticus, seizure-induced respiratory arrest (S-IRA), and Sudden Unexpected Death in Epilepsy (SUDEP). By "therapeutically effective amount" is meant the concentration of a compound that is sufficient to elicit the desired biological effect (e.g., treatment or prevention of epilepsy and associated symptoms and co-morbidities, including but not limited to seizure-induced sudden respiratory arrest (S-IRA). Diseases and conditions of interest include, but are not limited to, epilepsy, particularly intractable forms of epilepsy, including but not limited to Dravet syndrome, Lennox-Gastaut syndrome, Doose syndrome, infantile spasms, West syndrome, and other refractory epilepsies, as well as other neurological related diseases, obesity, and obesity-related diseases. Also of interest is the prevention or amelioration of symptoms and co-morbidities associated with those diseases In some embodiments, the subject method includes administering to a subject a compound to treat a neurological related disease. Neurological related diseases of interest include, but are not limited to, epilepsy, particularly severe or intractable forms of epilepsy, including but not limited to severe myoclonic epilepsy in infancy (Dravet syndrome), Lennox-Gastaut syndrome, Doose syndrome, infantile spasms, West syndrome, and other refractory epilepsies. In some embodiments, the subject method will be protective of symptoms, including but not limited to S-IRA, SUDEP, and co-morbid conditions.

Genetic Testing

In some cases, it can be desirable to test the patients for a genetic mutation prior to administration of some of the therapeutic agents provided by the disclosure, especially in cases where use of specific agent is contraindicated either because the agent is ineffective or because it would have undesired or serious side effects. Thus, it is in some cases desirable to test patients prior to treatment. In the case of patients having Dravet syndrome, testing can be carried out for mutations in the SCN1A (such as partial or total deletion mutations, truncating mutations and/or missense mutations e.g. in the voltage or pore regions S4 to S6), SCN1 B (such as the region encoding the sodium channel (β1 subunit), SCN2A, SCN3A, SCN9A, GABRG2 (such as the region encoding the γ2 subunit), GABRD (such as the region encoding the α subunit) and I or PCDH19 genes have been linked to Dravet syndrome.

Similarly, several reports in the literature evidence a strong, likely multifactorial genetic component for Doose syndrome (see e.g., Kelly et al., Developmental Medicine & Child Neurology 2010, 52: 988-993), and a number of mutations appear in a significant number of Doose syndrome patients, including sodium channel neuronal type 1 alpha subunit (SCN1A) mutations, sodium channel subunit beta-1 (SCN1B) and gamma-aminobutyric acid receptor, subunit gamma-2 (GABRG2) mutations; point mutations in exon 20 of SCN1A.

Other genetic tests can be carried out, and can be required as a condition of treatment.

Dosing

The different therapeutic agents disclosed herein can be dosed to patients in different amounts depending on different patient age, size, sex, condition as well as the use of different therapeutic agents.

For example, the dosing can be a daily dosing based on weight. However, for convenience the dosing amounts can be preset. In general, the smallest dose which is effective should be used for the particular patient. The patient can be dosed on a daily basis using a single dosage unit which single dosage unit can be comprised of the therapeutic agent in an amount appropriate for the particular agent. The dosage unit can be selected based on the delivery route, e.g. the dosage unit can be specific for oral delivery, transdermal delivery, rectal delivery, vaginal delivery, buccal delivery, intranasal and/or inhaled delivery, pulmonary delivery or delivery by injection.

Formulation

The dose of therapeutic agent administered in the methods of the present invention can be formulated in any pharmaceutically acceptable dosage form including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms; transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

Particular formulations of the invention are in a liquid form. The liquid can be a solution or suspension and can be an oral solution or syrup which is included in a bottle with a pipette which is graduated in terms of milligram amounts which will be obtained in a given volume of solution. The liquid solution makes it possible to adjust the solution for small children which can be administered in increments appropriate to the particular therapeutic agent.

Administration of the subject compounds can be systemic or local. In certain embodiments, administration to a mammal will result in systemic release of a subject compound (for example, into the bloodstream). Methods of administration can include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the subject compounds and compositions are administered orally. In certain embodiments, it can be desirable to administer a compound locally to the area in need of treatment. In some embodiments, the method of administration of the subject compound is parenteral administration. This can be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In some embodiments, the subject method includes administering to a subject an appetite suppressing amount of the subject compound to treat obesity. Any convenient methods for treating obesity can be adapted for use with the subject therapeutic agents. Any of the pharmaceutical compositions described herein can find use in treating a subject for obesity. Combination therapy includes administration of a single pharmaceutical dosage formulation which contains the subject compound and one or more additional agents; as well as administration of the subject compound and one or more additional agent(s) in its own separate pharmaceutical dosage formulation. For example, a subject compound and an additional agent active with appetite suppressing activity (e.g., phentermine or topiramate) can be administered to the patient together in a single dosage composition such as a combined formulation, or each agent can be administered in a separate dosage formulation. Where separate dosage formulations are used, the subject compound and one or more additional agents can be administered concurrently, or at separately staggered times, e.g., sequentially. In some embodiments, the method further includes co-administering to the subject with the subject therapeutic agent, an antiepileptic agent. Antiepileptic agents of interest that find use in methods of co-administering include, but are not limited to, Acetazolamide, Carbamazepine, (Tegretol), Onfi (Clobazam), Clonazepam (Klonopin), Lamotrigine, Nitrazepam, Piracetam, Phenytoin, Retigabine, Stiripentol, Topiramate, and Carbatrol, Epitol, Equetro, Gabitril (tiagabine), Keppra (levetiracetam), Lamictal (lamotrigine), Lyrica (pregabalin), Gralise, Horizant, Neurontin, Gabarone (gabapentin), Dilantin, Prompt, Di-Phen, Epanutin, Phenytek (phenytoin), Topamax, Qudexy XR, Trokendi XR, Topiragen (topiramate), Trileptal, Oxtellar (oxcarbazepine), Depacon, Depakene, Depakote, Stavzor (valproate, valproic acid), Zonegran (zonisamide), Fycompa (perampanel), Aptiom (eslicarbazepine acetate), Vimpat (lacosamide), Sabril (vigabatrin), Banzel, Inovelon (rufinamide), Cerebyx (fosphenytoin), Zarontin (ethosuximide), Solfoton, Luminal (phenobarbital), Valium, Diastat (diazepam), Ativan (lorazepam), Lonopin, Klonopin (clonazepam), Frisium, Potiga (ezogabine), Felbatol (felbamate), Mysoline (primidone).

In some embodiments, the subject method is an in vitro method that includes contacting a sample with a subject compound. The protocols that can be employed in these methods are numerous, and include but are not limited to, serotonin release assays from neuronal cells, cell-free assays, binding assays (e.g., 5-$HT_{2B}$ receptor binding assays); cellular assays in which a cellular phenotype is measured, e.g., gene expression assays; and assays that involve a particular animal model for a condition of interest (e.g., Dravet syndrome, Lennox-Gastaut syndrome, Doose syndrome, West syndrome, and other refractory epilepsies) or symptoms or comorbidities associated with such conditions.

Pharmaceutical Preparations

Also provided are pharmaceutical preparations. Pharmaceutical preparations are compositions that include a compound (either alone or in the presence of one or more additional active agents) present in a pharmaceutically acceptable vehicle. The term "pharmaceutically acceptable" means approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal.

The choice of excipient will be determined in part by the particular compound, as well as by the particular method used to administer the composition. Accordingly, there is a wide variety of suitable formulations of the pharmaceutical composition of the present invention.

The dosage form of a therapeutic agent employed in the methods of the present invention can be prepared by combining the therapeutic agent with one or more pharmaceutically acceptable diluents, carriers, adjuvants, and the like in a manner known to those skilled in the art of pharmaceutical formulation.

By way of illustration, the therapeutic agent can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions can contain common carriers and excipients, such as solubilizers, isotonic agents, suspending agents, emulsifying agents, stabilizers, preservatives, colorants, diluents, buffering agents, surfactants, moistening agents, flavoring agents and disintegrators, and including, but not limited to, corn starch, gelatin, lactose, dextrose, sucrose, microcrystalline cellulose, kaolin, mannitol, dicalcium phosphate, sodium chloride, alginic acid, vegetable or other similar oils, synthetic aliphatic acid glycerides, esters of higher aliphatic acids or propylene glycol, corn starch, potato starch, acacia, tragacanth, gelatin, glycerin, sorbitol, ethanol, polyethylene glycol, colloidal silicon dioxide, croscarmellose sodium, talc, magnesium stearate and stearic acid. Disintegrators commonly used in the formulations of this invention include croscarmellose, microcrystalline cellulose, corn starch, sodium starch glycolate and alginic acid. The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

In some cases, the compound is formulated for oral administration. In some cases, for an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition can be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition can also contain minor amounts of non-toxic auxiliary substances such as wetting agents, emulsifying agents, or buffers.

Particular formulations of the invention are in a liquid form. The liquid can be a solution or suspension and can be an oral solution or syrup which is included in a bottle with a pipette which is graduated in terms of milligram amounts which will be obtained in a given volume of solution. The liquid solution makes it possible to adjust the solution for small children which can be administered anywhere from 0.5 mL to 15 mL and any amount between in half milligram increments and thus administered in 0.5, 1.0, 1.5, 2.0 mL, etc.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a powder for reconstitution.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Several selective serotonin (5-HT) reuptake inhibitors were found to prevent seizure-induced respiratory arrest (S-IRA) in DBA mice. However, not all drugs that enhance the activation of 5-HT receptors effectively block S-IRA in DBA mice. Therefore, fenfluramine (FFA) was investigated to determine whether its augmentation of 5-HT release altered susceptibility to audiogenic seizures and S-IRA in DBA/1 mice.

Example 1

Effects of Fenfluramine on Animal Model of SUDEP

Materials and Methods

Animals

These studies involved age matched (<80 days) male DBA/1 mice obtained from ENVIGO. Because there were no significant sex differences in the AGSz incidence (frequency), severity and S-IRA susceptibility in DBA/1 mice, males were used in this study. The mice were primed as described in previous studies (Faingold et al., (2010). *Epilepsy Behav.* 17:436-40; Faingold, et al. (2011) *Brain Res.* 1418:104-10; Faingold, et al., (2011) *Epilepsy Behav.* 22:186-90). Briefly, the mice were maintained on an ad libitum diet under a 12 h light-dark cycle in a temperature and humidity-controlled laboratory animal medicine facility. Starting at postnatal day 23-25, the mice were primed and tested for consistent susceptibility to AGSz and S-IRA by presenting an intense acoustic stimulus, as described previously. The mice exhibiting consistent susceptibility to S-IRA on three consecutive tests were included in the following studies.

Seizure Induction and Resuscitation

AGSz were induced by presenting to each DBA/1 mouse (N=287) an intense (110 dB SPL; re: 0.0002 dynes/cm$^2$) broad-band acoustic stimulus from an electrical bell (Heath Zenith Model #172C-A) installed inside a plastic cylinder (43 cm diameter). using an electrical bell, and resuscitation was accomplished using a rodent respirator (Faingold et al., (2010) DBA/1 mice exhibit chronic susceptibility to audiogenic seizures followed by sudden death associated with respiratory arrest. *Epilepsy Behav.* 17:436-40).

The stimulus was presented until the mouse exhibited tonic seizures or for a maximum duration of 60 s. The typical seizure semiology in the DBA/1 mice begins with a wild running phase, followed by clonic-tonic seizures and then tonic hind-limb extension that immediately leads to S-IRA during post-ictal behavioral depression (PID). The onset of S-IRA was visually determined by the occurrence of respiratory failure following loss of the righting reflex, relaxation of the pinnae, and then a generalized loss of muscle tone. These behaviors are reliable indicators of imminent sudden death in DBA mice. Resuscitation was initiated within 10 s after pinna relaxation and the generalized loss of muscle tone, which was effective in reversing S-IRA and reviving >90% of the mice. The mice were placed in a supine position, and a polyethylene tube (4.4 mm external diameter) connected to the outflow of a rodent respirator (Harvard Apparatus 680), pumping one cc of room air at 200 strokes/min, was the placed over the nostrils, which produced observable displacement of the chest. Respiratory support was provided until spontaneous breathing rhythm returned, which required ~19 sec. The mice were monitored until they regained the righting reflex and then returned to their home cage. Video recordings of seizure behaviors and recovery were made for off-line evaluation and analysis, including the duration of PID, as indicated by time from muscle tone loss to return of the righting reflex.

Behavioral Testing

The experiments herein disclosed examined the dose-response relationship of FFA (10-40 mg/kg, i.p.) on AGSz-induced behaviors in DBA/1 mice compared to vehicle (saline) treated control mice using different seizure-testing protocols. This initial protocol involved induction of AGSz at 30 min, 12 h and 24 h after drug administration, and subsequently at 24 h intervals until susceptibility to S-IRA returned. These studies were aimed at determining whether FFA can reduce the incidence (frequency) and severity of AGSz and susceptibility to S-IRA. Based on these results, the 5-20 mg/kg dose range was selected to determine the time-course of FFA's effect in another group of DBA/1 mice by a second seizure testing protocol using 8 h intervals during the first 24 h to evaluate the time course of effect in greater detail, and subsequently at 24 h periods. To determine the effect of FFA on the severity of AGSz in DBA/1 mice, the ordinal scoring system of De Sarro and coworkers was used: no seizure=0; wild running=1; clonic seizure=2; tonic seizure=3; death/S-IRA=4. The median effective dose ($ED_{50}$) for FFA for blocking AGSz at 30 min following the i.p. injection in DBA/1 mice was calculated using a second order polynomial equation ($y=65.113x^2-2.0715x-63.578$) that gave the best fit ($R^2=0.9989$).

Drugs

Fenfluramine (FFA), kindly provided by Zogenix International, was dissolved in sterile saline vehicle prepared in the laboratory using Sodium Chloride tablets (Catalog number: 07982-100TAB-F) obtained from Sigma-Aldrich (St. Louis, Mo., U.S.A.).

Statistical Analysis

The videos of seizure behaviors were analyzed visually, and the incidence (frequency) of AGSz, seizure severity, and incidence (frequency) of S-IRA following drug treatment were compared statistically to vehicle controls using the Chi-square, Mann-Whitney U or paired samples t-test with SPSS software. The $ED_{50}$ was calculated using SigmaPlot 13 and Microsoft® Excel. The experimental protocols used in these studies were approved by the Laboratory Animal Care and Use Committee of Southern Illinois University School of Medicine, which are in accordance with National Institutes of Health guidelines for the care and use of laboratory animals. Measures to minimize animal usage as well as pain and discomfort were included in these procedures.

Dose- and Time-Dependent Anticonvulsant Effect of FFA on Audiogenic Seizures (AGSz) in DBA/1 Mice.

Administration of FFA resulted in blockade of AGSz in a dose- and time-dependent manner in DBA/1 mice. Using an initial testing paradigm susceptibility to AGSz was significantly reduced following 20 and 40 mg/kg FFA (p<0.01 and p<0.001 respectively, Chi-square test) at 30 minutes when compared to saline-treated controls (FIG. 1A). Regarding FIG. 1A, which shows the effect of FFA on AGSz, systemic intraperitoneal (i.p.) injection of FFA at: 15 mg/kg (light vertical line bars; n=9), 20 mg/kg (large confetti dotted bars; n=11) and 40 mg/kg (large diagonal stripe; n=6) was observed to significantly reduce the incidence (frequency) of AGSz compared to saline treated control mice (solid black bars; n=21). No significant effect on AGSz incidence (frequency) was seen in the mice that received 10 mg/kg (wide downward diagonal line bars; n=11) FFA. [*p<0.05; **p<0.01; #p<0.001 indicate statistically different from controls, respectively, as determined by Chi-square test].

Figure 1B:
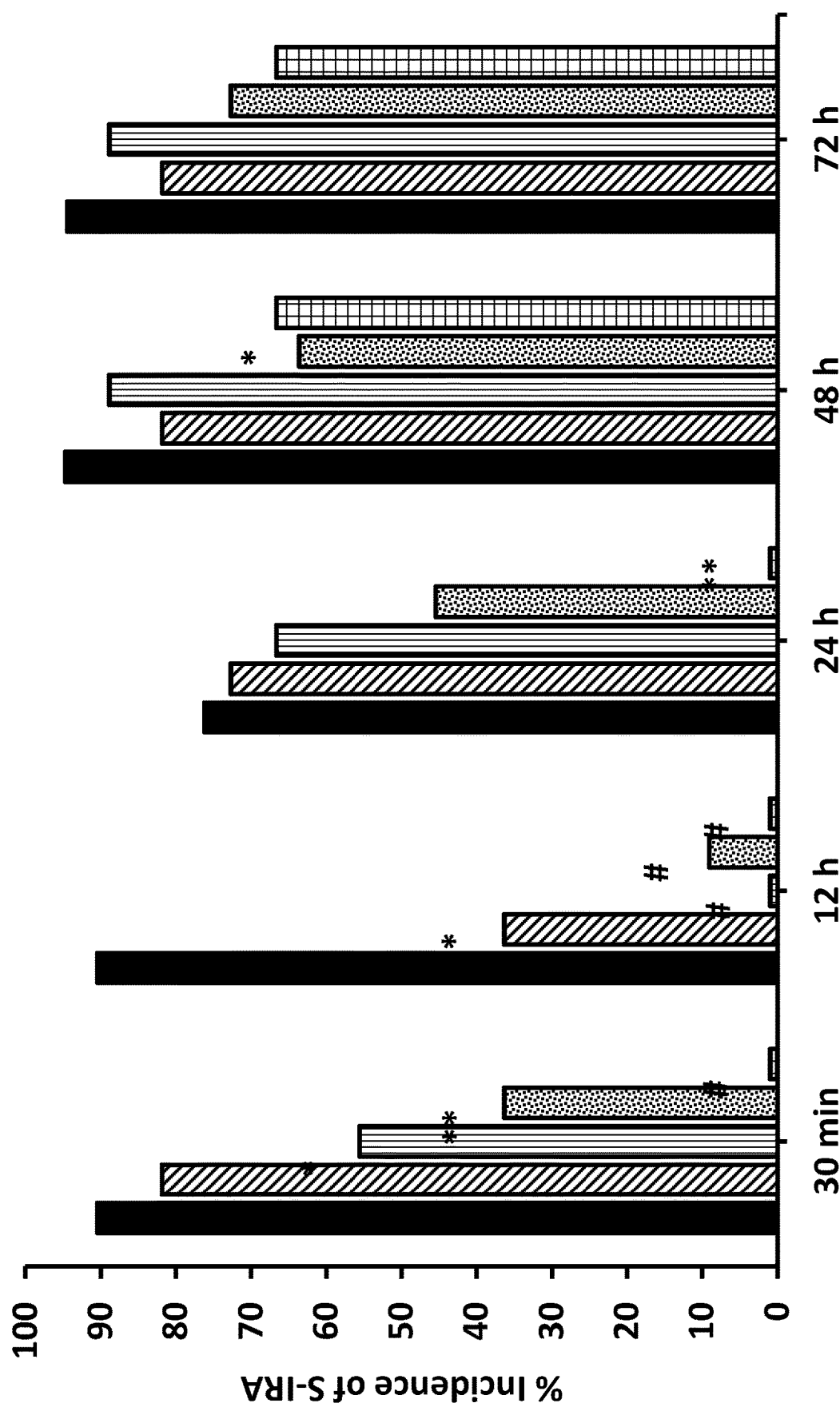

FIG. 1B shows the effect of FFA in preventing S-IRA following AGSz in DBA/1 mice. A significant reduction in the incidence (frequency) of S-IRA, which began at 30 min, was seen in mice that received 15, 20 and 40 mg/kg intraperitoneal FFA compared to saline treated controls (bars coded as above). The incidence (frequency) of S-IRA in the mice that received 10 mg/kg FFA was not affected. A significant return of S-IRA susceptibility in the FFA-treated DBA/1 mice occurred by 72 h. [*p<0.05; **p<0.01; #p<0.001 indicate statistically different from controls, respectively, as determined by Chi-square test].

The effect of FFA was relatively long-lasting, since it was still significant at 24 h. The frequency of seizure was no longer significantly different from the control group at 48 h. The mice that received 15 mg/kg of FFA showed a relatively shorter duration (<24 h) and later onset of AGSz blockade at 12 h (p<0.01, Chi-square test). In this testing paradigm, the 10 mg/kg dose of FAA was ineffective in blocking AGSz. The $ED_{50}$ for blockade of AGSz by FFA at 30 min was 21.7 mg/kg (FIG. 1C). FIG. 1C: Median effective dose ($ED_{50}$), as illustrated by the intercept for 50% efficacy, was determined by plotting log doses 10, 15, 20 and 40 mg/kg of FFA against the percent incidence (frequency) of AGSz in DBA/1 mice at 30 min following FFA treatment.

Figure 1D:
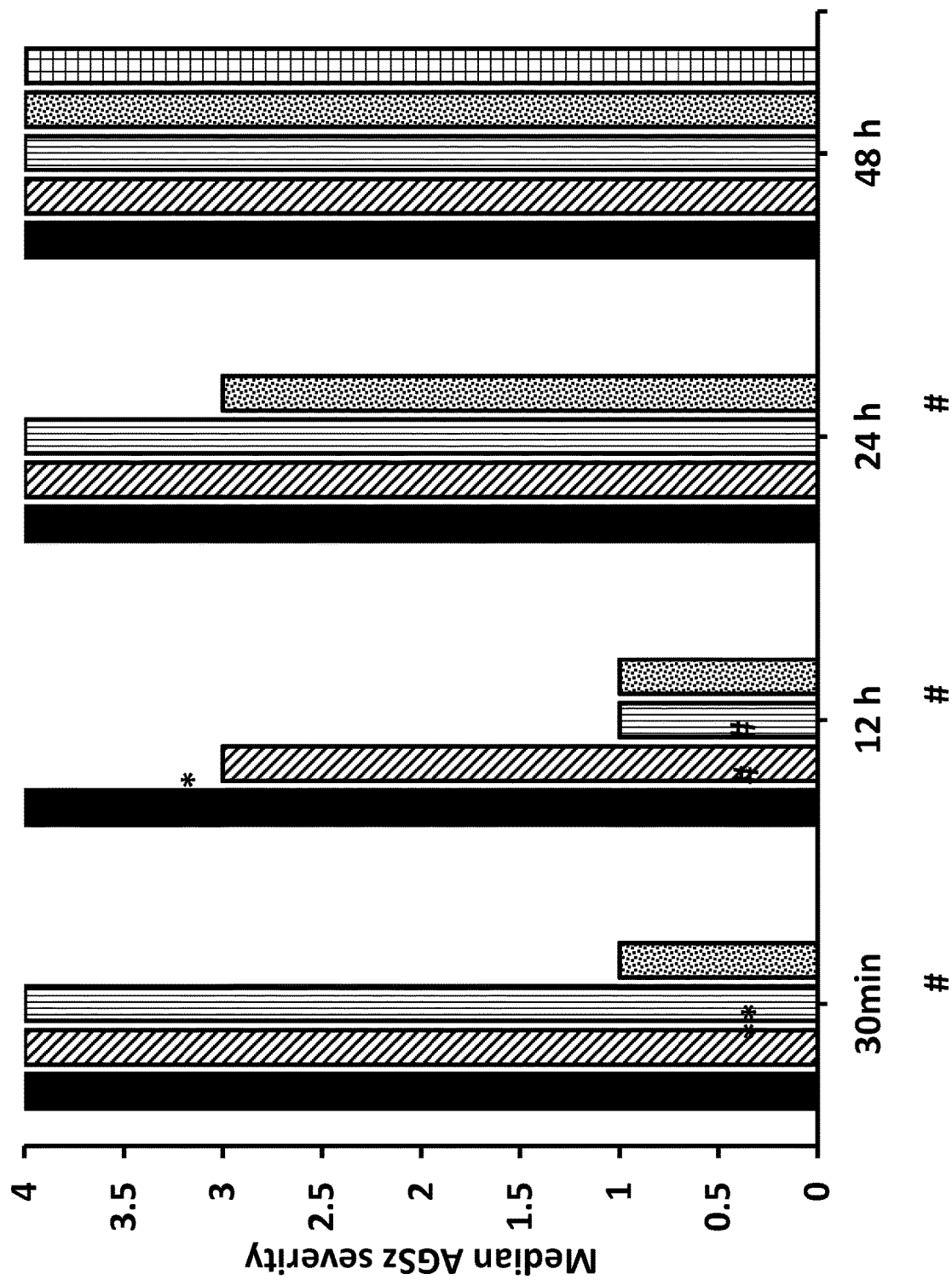
Figure 5:
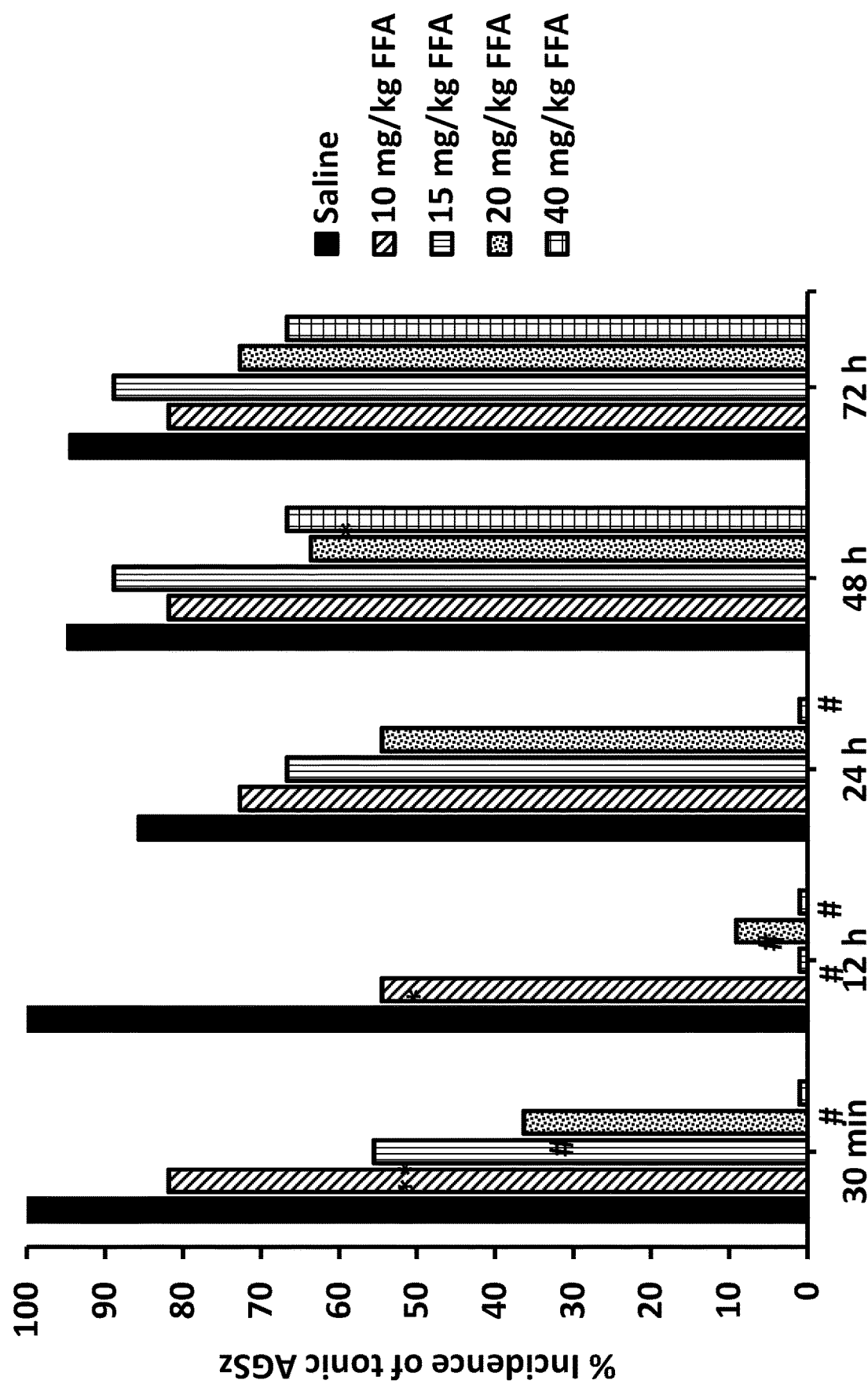
FIG. 5: shows that FFA significantly reduced the incidence (frequency) of tonic seizures, the AGSz phenotype known to lead to S-IRA in the DBA/1 mouse model of SUDEP.

FFA also significantly reduced AGSz severity in DBA/1 mice. The AGSz severity reduction data, based on the severity score, mirrored the incidence (frequency) data described above. The early onset of significantly reduced AGSz severity (30 min) was seen in mice that received 20 or 40 mg/kg FFA, and the return of maximal seizure severity occurred at 24 h and 48 h, respectively (FIG. 1D). As shown in FIG. 1D: FFA effectively reduced the severity of AGSz in DBA/1 mice; starting at 30 min following 20 and 40 mg/kg of FFA (i.p), a significant reduction in the median AGSz severity score was observed when compared to saline treated controls. In the case of mice that received 10 and 15 mg/kg FFA, the reduction in severity score was delayed and occurred at 12 h. A significant return of AGSz severity in the FFA treated DBA/1 mice occurred by 48 h. [*p<0.05; p<0.01; #p<0.001 indicate statistically different from controls, respectively, as determined by Mann-Whitney U test]. The AGSz severity reduction in mice that received 15 mg/kg FFA was shorter in duration with a later onset, occurring at 12 h, which was similar to the seizure incidence data (FIG. 1A). At 10 mg/kg, FFA significantly reduced AGSz severity (but not seizure incidence/frequency) in DBA/1 mice at 12 h (p<0.05, Mann-Whitney U test). The effect of 10 mg/kg of FFA on AGSz severity was no longer present by 24 h. the blockade of S-IRA by FFA (FIG. 1B) was found to coincide with reduction in tonic seizure incidence (FIG. 5). The incidence of S-IRA following AGSz in DBA/1 mice was significantly reduced (p<0.05, Chi-square test) by 15-40 mg/kg of FFA at 30 min after administration. The effect on S-IRA and tonic seizure incidence following a single systemic injection at the 40 mg/kg dose was long-lasting. Although the tonic AGSz and S-IRA susceptibility returned by 72 h in the mice that received 40 mg/kg FFA, 33.3% of these mice continued to show a reduced susceptibility to these seizure behaviors for up to 8 days. In contrast, the mice that received 10 mg/kg of FFA showed a shorter-duration and a later onset of the reduction of S-IRA (36.4%) and tonic seizure (54.6%) at 12 h ($p<0.01$, Chi-square test). Even though, under this testing paradigm, 18.2% mice that received 10 mg/kg FFA showed S-IRA blockade following tonic seizure at 12 h (FIG. 1B and FIG. 5), the incidence of this selective S-IRA blocking effect was not statistically significant. As can be seen in FIG. 5, FFA significantly reduced the incidence of tonic seizures, the AGSz phenotype known to lead to S-IRA, in DBA/1 mice. Starting at 30 min following 20 mg/kg FFA (large confetti dotted bars; n=11) and 40 mg/kg FFA (large grid; n=6) intraperitoneally administered, a significant reduction in tonic seizure incidence was seen compared to saline treated controls (solid black bars; n=21). This tonic seizure blocking effect was delayed and transient in the mice treated with 15 mg/kg FFA (light vertical line bars; n=9). The incidence of tonic seizures in 10 mg/kg FFA (wide downward diagonal line bars; n=11) treated mice was not affected. A significant return of S-IRA susceptibility among the FFA treated DBA/1 mice occurred by 72 h. r$p<0.05$; $p<0.01$; #$p<0.001$ indicate statistically different from controls, respectively, as determined by Chi-square test).

Effects of FFA Under the 8-Hour Testing Protocol

Figure 2A:
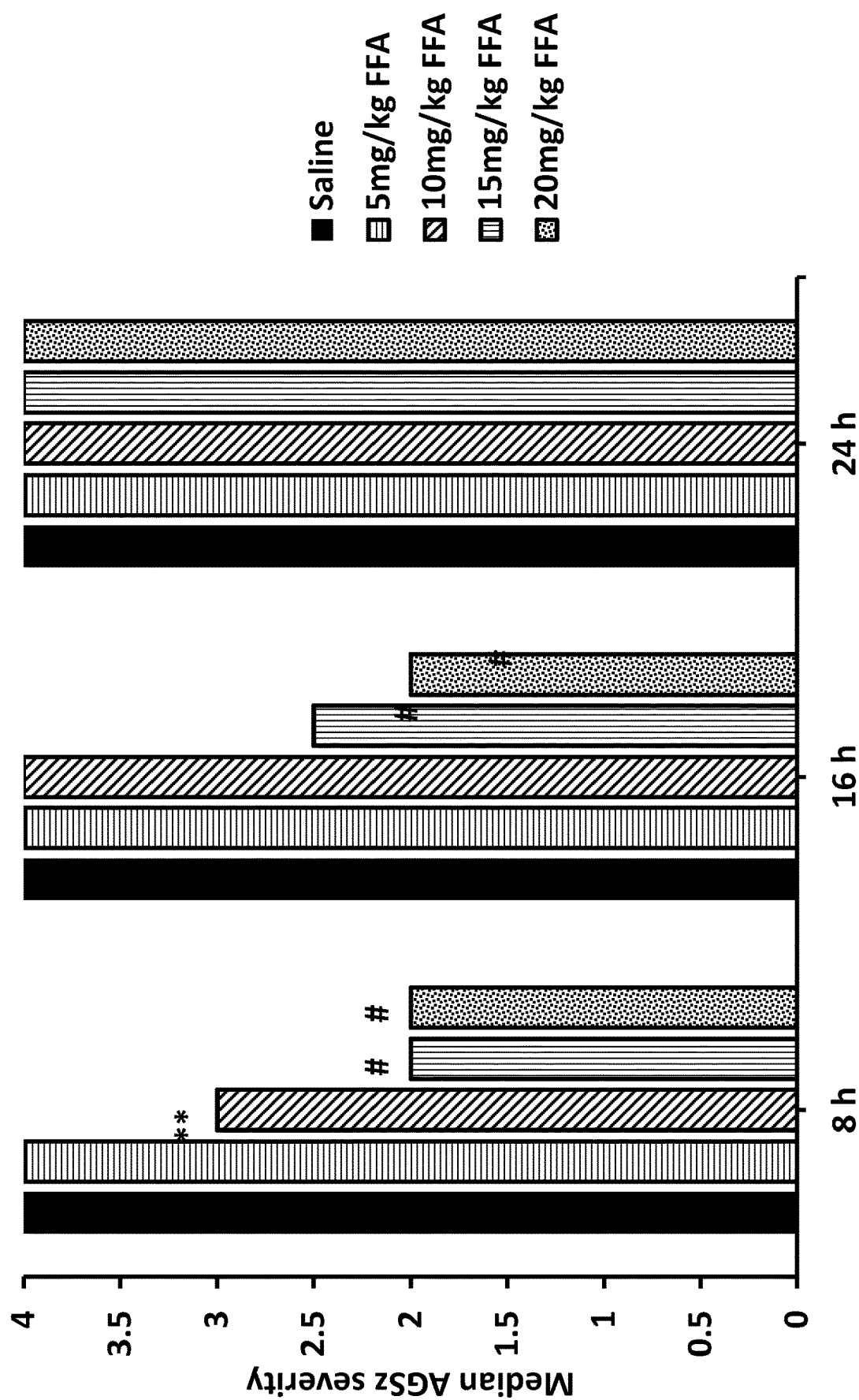
FIG. 2A-2D: show a time-course of selective seizure-induced respiratory arrest (S-IRA) blocking effect of FFA in DBA/1 mice (8 h testing protocol).

FIGS. 2A through 2D show a time-course of selective S-IRA blocking effect of FFA in DBA/1 mice (8 h testing protocol). The 8-h testing protocol during the first 24 h was employed in the next group of studies of the effect of 5-20 mg/kg (i.p.) doses of FFA. A significant ($p<0.01$, Mann-Whitney U test) reduction in the median severity scores of AGSz was seen with 10-20 mg/kg doses of FFA at 8 h (FIG. 2A), and AGSz severity returned to pre-drug levels by 24 h, which is similar to the results with the initial testing protocol (FIG. 1D). As shown in FIG. 2A, FFA reduced the AGSz severity in DBA/1 mice. Mice receiving i.p. injection of 10 mg/kg FFA (wide downward diagonal line bars; n=10), 15 mg/kg FFA (light vertical line bars; n=10) and 20 mg/kg FFA (large confetti dotted bars; n=9) showed a significant reduction in the median AGSz severity scores compared to saline treated controls (solid black bars; n=12) starting at 8 h during the time-course study. The severity of AGSz remained unaffected in the mice that received 5 (light horizontal line bars; n=9) mg/kg FFA. A significant return of AGSz severity among the FFA treated DBA/1 mice occurred by 24 h. [**$p<0.01$; #$p<0.001$ indicate statistically different from controls, Mann-Whitney U test].

Figure 2B:
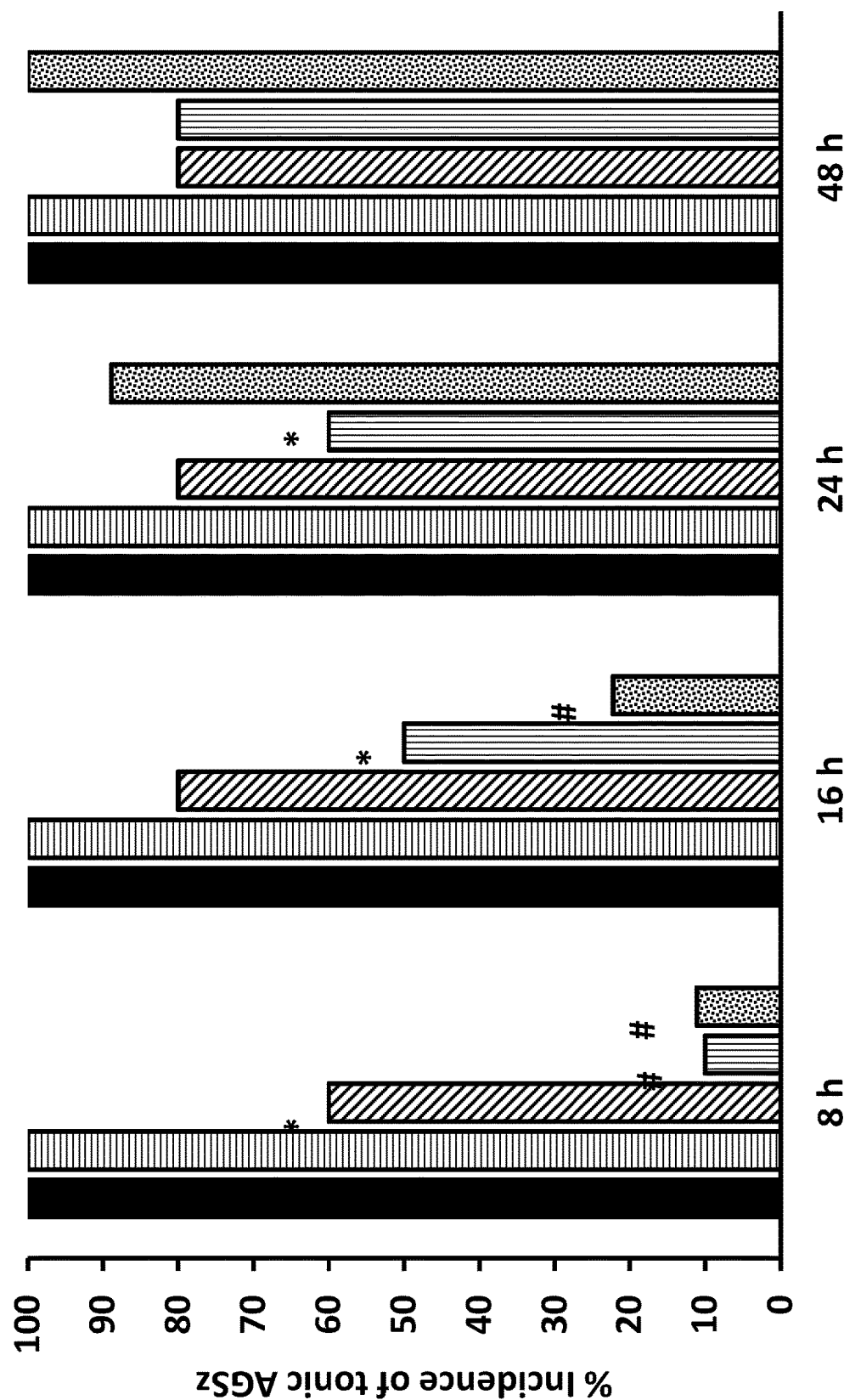

As shown in FIG. 2B: FFA reduced the incidence of tonic seizures, which can result in S-IRA, in DBA/1 mice. The incidence of tonic seizures, which precede S-IRA in DBA/1, was significantly reduced in mice that received 10-20 mg/kg of FFA at 8 h compared to saline treated controls (FIG. 2B). A significant reduction in the incidence of the tonic seizure was seen at 8 h in DBA/1 mice that received 10, 15 and 20 mg/kg FFA. This effect of FFA was found to be reversed by 48 h. It was observed that the return of susceptibility to tonic seizures occurred between 16-48 h in mice that received 10-20 mg/kg doses of FFA. The dose of 5 mg/kg FFA was ineffective against the tonic seizures in DBA/1 mice. [*$p<0.05$; #$p<0.001$ indicate statistically different from saline treated controls, respectively, as determined by Chi-square test].

Figure 2C:
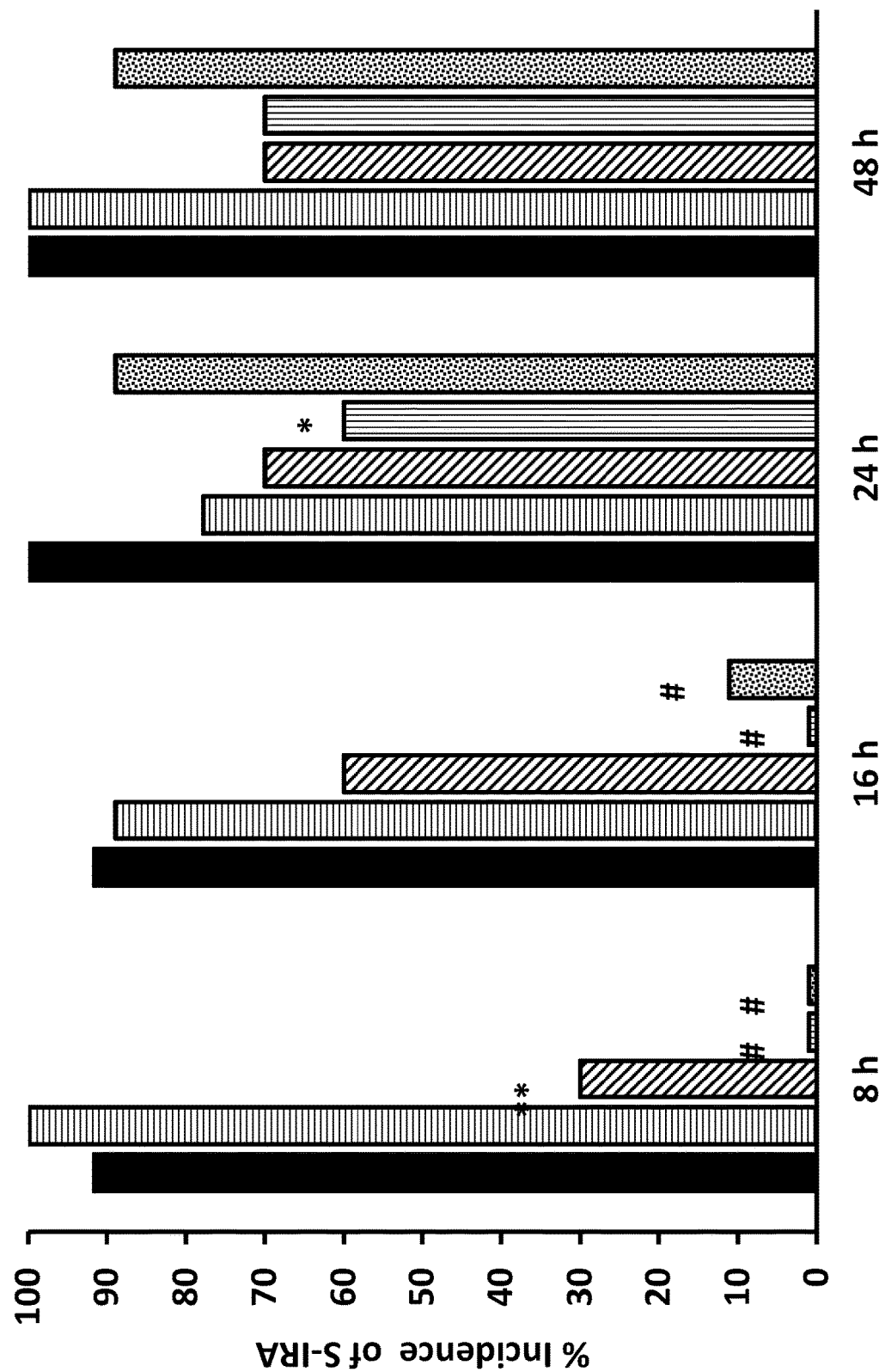

FFA prevented S-IRA in DBA/1 mice. The mice that received 10-20 mg/kg of FFA showed a significant reduction in the incidence of S-IRA starting at 8 h (FIG. 2C). Starting at 8 h following 10, 15 and 20 mg/kg FFA, a significant reduction in the incidence of S-IRA occurred when compared to saline treated controls. The incidence of S-IRA in the mice that received 5 mg/kg FFA was not affected. The reduction in S-IRA incidence under this paradigm mostly coincided with a significant reduction in the incidence of tonic AGSz susceptibility (see FIG. 2B). A return of S-IRA susceptibility among the FFA treated DBA/1 mice occurred at 48 h. [*$p<0.05$; **$p<0.01$; #$p<0.001$ indicate statistically different from controls, respectively, as determined by Chi-square test].

Figure 2D:
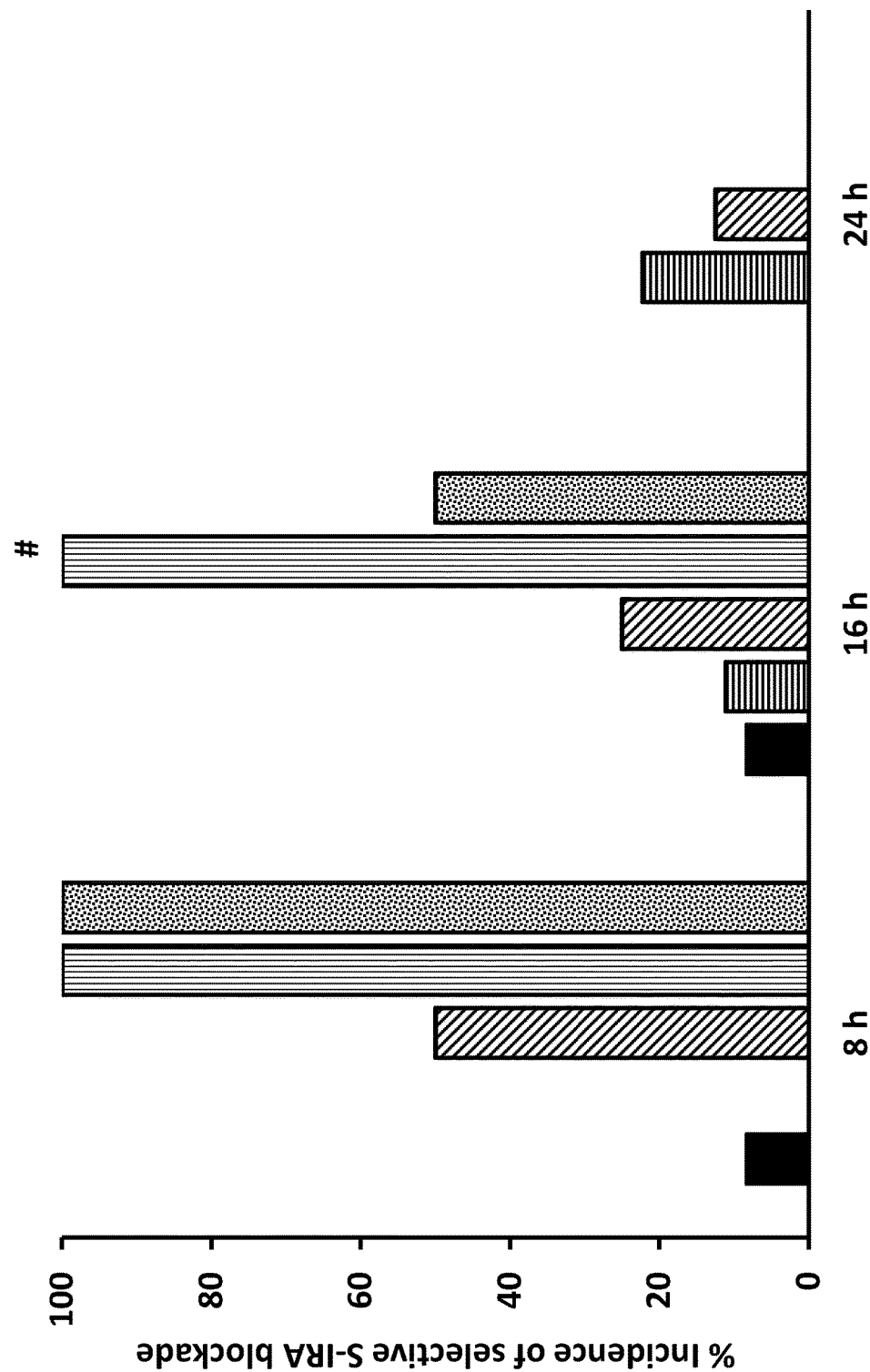

FIG. 2D shows selective S-IRA blocking effect of FFA. A significant reduction in the incidence of S-IRA was seen at the 16 h time point in 100% of the mice (n=5) that showed tonic AGSz following 15 mg/kg FFA, and continued to exhibit tonic seizures displayed a significant [#$p<0.001$, Chi-square test] incidence of selective blockade of S-IRA (FIG. 2B-2D). A return of susceptibility to S-IRA following AGSz in these FFA-treated mice was seen by 48 h.

Figure 6:
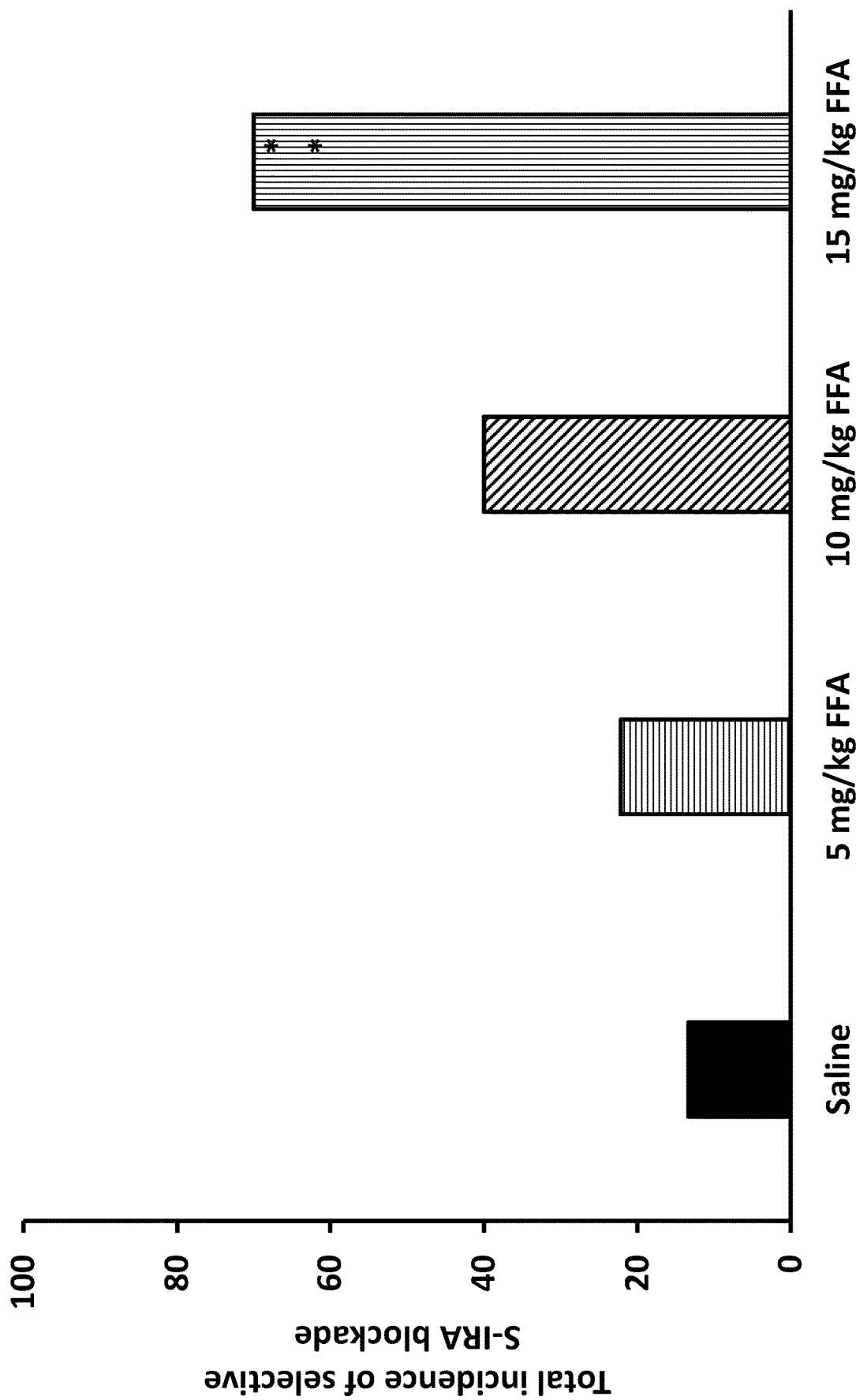
FIG. 6: shows the total incidence (frequency) of selective S-IRA blockade seen in DBA/1 mice treated with 5, 10 and 15 mg/kg intraperitoneal FFA using an 8-hour testing protocol.

Referring to FIG. 6, the total incidence of selective S-IRA blockade seen in DBA/1 mice was 70% during these time-course studies (FIG. 6). In the DBA/1 mice treated with FFA, the total incidence of selective S-IRA blockade is shown in FIG. 6; mice treated with 5 mg/kg FFA i.p. (light horizontal line bars; n=9), 10 mg/kg FFA i.p. (wide downward diagonal line bars; n=10) and 15 mg/kg FFA i.p. (light vertical line bars; n=10) under the 8-h testing protocol. [** $p<0.01$ indicates statistically different from saline treated controls (solid black bars; n=12), Chi-square test]. The mice that were treated with 20 mg/kg FFA followed a similar trend, but the incidence of both S-IRA and tonic seizure blockade occurred in most of these mice (FIG. 2B-2C). The dose of 5 mg/kg of FFA was ineffective in blocking any AGSz behavior in the DBA/1 mice.

Figure 3:
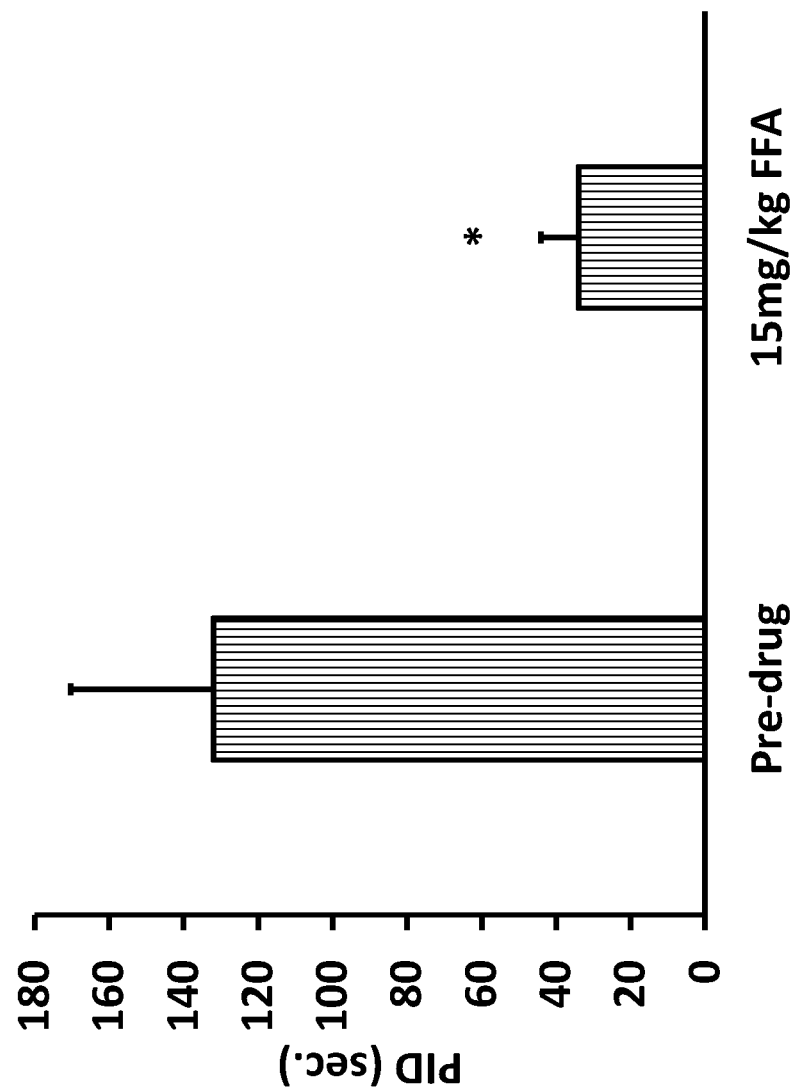
FIG. 3: shows selective S-IRA blockade by 15 mg/kg (n=10) FFA, associated with significant reduction in mean post-ictal depression (PID) period, as defined by duration of righting reflex loss, compared to last priming test duration (pre-drug).

FIG. 3 shows selective S-IRA blockade by 15 mg/kg FFA (n=10) is associated with significant reduction in mean post-ictal depression (PID) period, as defined by duration of righting reflex loss, compared to their last priming test duration (pre-drug). [*$p<0.05$ (Paired-samples t-test)]. The duration of the loss of righting reflex following AGSz in DBA/1 mice is a measure of PID, which is a contributing factor to SUDEP in patients. The duration of PID (34.6±13.3 s) at 16 h after 15 mg/kg of FFA in those mice that showed selective S-IRA blockade was significantly reduced ($p<0.05$, paired t-test) when compared to their last priming seizures (168.6±43.4 s) (FIG. 3).

FIGS. 4A and 4B illustrate the reduction in the incidence of severe seizures and prevention of S-IRA by FFA pretreatment. In subsequent experiments, AGSz were examined in DBA/1 mice that were treated with 15 mg/kg of FFA i.p. but were initially tested at 16 h. FIG. 4A: The DBA/1 mice tested for the first time at 16 h following 15 mg/kg FFA (n=73) showed a significant reduction in the overall incidence of tonic seizures (68.5%) and S-IRA (21.9%) as compared to their saline treated controls (n=38) (FIG. 4A). FIG. 4B shows a significant incidence of selective S-IRA blockade (68%) among the DBA/1 mice that continued to display tonic seizures at 16 h following treatment with 15 mg/kg FFA (n=50) compared to their saline treated controls. [#$p<0.001$ (Chi-square test] (FIG. 4B). The return of S-IRA susceptibility (94.5%) in the FFA treated mice occurred at 48 h consistent with the previous findings (FIG. 2C).

Discussion

The present study found that FFA administration significantly reduced seizure severity or blocked AGSz susceptibility in DBA/1 mice in a dose- and time-dependent manner. FFA was also found to significantly reduce the incidence of S-IRA, and a selective block of S-IRA without affecting any seizure behavior was also observed. These findings suggest that FFA has the therapeutic potential for improving seizure control and preventing SUDEP.

This is the first study examining the anticonvulsant effect of FFA in a mammalian model of epilepsy and SUDEP. FFA reduced the incidence of tonic seizures, which is considered to be the most severe type of seizure that often leads to S-IRA, and also reduced the susceptibility to AGSz in DBA/1 mice, depending on the dose. These effects are consistent with the significant reduction in seizure frequency observed with add-on (adjunctive) FFA therapy in Dravet syndrome patients, which is a form of pediatric epilepsy that exhibits a great degree of pharmaco-resistance as well as a very high incidence of SUDEP. Clinical studies in Dravet syndrome patients found that add-on therapy with drugs that enhance serotonin receptor activation, including FFA, resulted in a significant reduction in seizure frequency.

The anticonvulsant effect of a single administration of FFA against AGSz in DBA/1 mice in the present study was long-lasting. This finding is consistent with rat studies in which similar FFA doses exerted central serotonergic effects lasting for one week. This sustained effect of FFA is likely due, in part, to its active metabolite, N-FFA. A relatively prolonged anticonvulsant effectiveness (ending by 72 h) was seen in studies with fluoxetine, which is also thought to be mediated, at least in part, by its active metabolite, norfluoxetine. However, the seizure severity decrease in DBA/1 mice with the 40 mg/kg dose of FFA was more prolonged, lasting for up to 8 days, and the basis for this extended duration will require further study.

DBA/1 mice show consistent susceptibility to sudden death due to S-IRA immediately following AGSz unless resuscitation is rapidly provided. In the present study FFA exerted a significant dose- and time-dependent blockade of S-IRA and AGSz. A more detailed investigation into the time-course of the effect of FFA with testing at 8 h intervals revealed that 15 mg/kg of FFA induced a significant and selective blockade of S-IRA without blocking any seizure behavior in the DBA/1 mice at 16 h (FIG. 2D). The overall incidence of selective S-IRA blockade was 70% in this group of mice (FIG. 6), and 15 mg/kg of FFA was also found to reduce the duration of PID significantly (FIG. 3), which may also be important, since prolonged PID is a major SUDEP risk factor. The significant incidence of selective S-IRA blockade was also seen in the mice that were tested initially at 16 h following 15 mg/kg of FFA (FIG. 4B), further confirming the effectiveness of the drug and the time-course of the effect. Preliminary pharmacokinetic experiments in DBA/1 mice of the FFA doses used in this study indicate that the plasma level of FFA at 16 h after the 15 mg/kg dose as well as its area under the curve were comparable to the levels observed in Dravet syndrome patients following a single oral dose (0.8 mg/kg) of FFA. Furthermore, the dose of 15 mg/kg FFA in adult mouse, based on body surface areas in accordance with Reagan-Shaw and co-workers, translates to the clinically effective range [1.8 mg/kg/day (child) or 1.2 mg/kg/day (adult)] used in patients. The presently disclosed FFA doses are also similar to those in the rodent studies, which established the original usefulness of this drug.

Thus, sixteen hours after administration of 15 mg/kg of FFA, a selective blockade of S-IRA occurred with no significant change in any seizure behavior in DBA/1 mice. Thirty min after 20-40 mg/kg of FFA, significant reductions of seizure incidence and severity as well as S-IRA susceptibility occurred, which were long-lasting (≥48 h). The median effective dose ($ED_{50}$) for significantly reducing AGSz at 30 min after FFA injection was 21.7 mg/kg.

The present disclosure provides evidence for the effectiveness of FFA against seizures and seizure-induced death in a mammalian SUDEP model. The ability of a low FFA dose to block S-IRA selectively suggests the potential usefulness of FFA in prophylaxis of SUDEP. These results further confirm and extend the serotonin hypothesis of SUDEP.

Systemically administered FFA in DBA/1 mice is effective in preventing S-IRA and also exerts a long-lasting and dose-dependent anticonvulsant effect. These findings with FFA, which is known to augment central serotonin release, are consistent with findings using fluoxetine, which enhances the action of serotonin by selectively blocking re-uptake. As mentioned earlier, death following AGSz in DBA/1 mice results from respiratory failure. Serotonin normally plays an important modulatory role in mediating state-dependent changes in the respiratory drive and activity in the brainstem stem respiratory centers. Brainstem raphe neurons are the major source of brain serotonin, and recent neuroimaging studies indicate that significant activity changes occur in specific raphe nuclei as a result of S-IRA in DBA/1 mice. Deletion of central serotonergic neurons resulted in reduced arousal and deficits in respiratory responses to elevated $CO_2$ levels in transgenic rodents. DBA/1 mice exhibit a genetic deficiency of serotonin synthesis due to reduced expression of tryptophan hydroxylase 2. Dietary supplementation with 5-hydroxytryptophan, a precursor of serotonin synthesis, significantly reduced the incidence of AGSz behaviors and blocked S-IRA in DBA/1 mice. In addition, significantly reduced $5-HT_{2C}$ and $5-HT_{3B}$ receptor expression occurs in DBA/1 mice, and the action of fluoxetine to block S-IRA in DBA/1 mice is mediated, in part, by $5-HT_3$ receptors. In addition to confirming our initial studies in DBA/1 mice, the present findings also extend the evidence for the anticonvulsant and potential SUDEP-preventing effects of enhancing central serotonergic neurotransmission. The importance of serotonin in epilepsy and SUDEP is also supported by the recent study, which found that FFA was effective in preventing both behavioral and electrographic epileptiform activity in a zebrafish model of Dravet syndrome. Recent autopsy findings in human SUDEP cases also show serotonergic abnormalities in brainstem nuclei, including the raphe nuclei. (Patodia, et al., The ventrolateral medulla and medullary raphe in sudden unexpected death in epilepsy. *Brain*. Epub 2018 Mar. 28). Taken together, these findings suggest the potential usefulness of FFA in the prevention of SUDEP in patients.

In summary, SUDEP prophylaxis and better seizure control are promising new uses for fenfluramine, previously been marketed for weight loss. Repurposing of drugs has been credited for rapid identification and translation from bench to bedside in many fields of medicine, including epilepsy. The specific brain regions and serotonin receptor types that are involved in mediating S-IRA and seizure blocking effect of FFA may be determined. In addition to serotonergic system, FFA is also known act on sigma and adrenergic receptors. The role of these actions and determination of the cerebrospinal fluid levels of serotonin and other monoamines may offer insights into the mechanism(s) of the effect of FFA and also the pathogenesis of seizure-induced death. Because the chronic addition of FFA was found to be effective in Dravet syndrome patients, a detailed investigation of the effect of continued treatment will provide further evidence of the anticonvulsant and SUDEP prophylaxis potential of FFA.

Example 2

Using Serotonin (5-HT) Antagonists to Characterize Activity of Fenfluramine in Mouse Model of SUDEP and Dravet Syndrome Recently, the contributions of several serotonin receptor subtype(s) in mediating the action of fenfluramine in blocking seizure-induced sudden death were evaluated in the DBA/1 mouse model of SUDEP. In these studies, fenfluramine, known to enhance the release of serotonin (5-hydroxytryptamine, 5-HT) in the brain, was found to be effective in blocking audiogenic seizures (AGSz) and seizure-induced respiratory arrest (S-IRA) in DBA/1 mice (data not shown). However, before the present disclosure, it was unknown whether fenfluramine's effect was mediated by specific 5-HT receptors. Thus, as is presently disclosed, several 5-HT receptor-specific antagonists were used to investigate fenfluramine's effect, to determine whether the antagonists could reverse the anticonvulsant activity (or any other effect) mediated by fenfluramine, and identify a subset of 5-HT receptors to which fenfluramine binds and acts as an agonist.

The efficacy of several 5-HT antagonists in reversing fenfluramine's effect on AGSz in DBA/1 mice have been evaluated. Antagonists of 5-HT$_{1a}$, 5-HT$_2$, 5-HT$_3$, 5-HT$_4$, 5-HT$_{5a}$ and 5-HT$_7$ receptors were tested and the results are detailed below. Studies investigating the effect of 5-HT$_6$ and 5-HT$_{1a/1b}$ antagonists are underway.

For these experiments, DBA/1 mice were used (after subjecting to the established priming procedure to assure consistent susceptibility to S-IRA following AGSz) to assess the effects of fenfluramine on various 5-HT receptors. Seizures were induced using an electrical bell, and resuscitation was accomplished using a rodent respirator (Faingold et al., 2010). At least 24 hours after priming, the mice received FFA (15 mg/kg, i.p.) and were tested for AGSz and S-IRA susceptibility 16 hours later. Thirty minutes prior to AGSz induction, a selective 5-HT receptor antagonist or vehicle was administered to evaluate if a specific receptor contributes to the ability of FFA to block S-IRA. Seizure behaviors were recorded on videotape, quantified, and compared statistically with vehicle-treated negative and FFA-treated positive controls (Chi-Square Test; significance set at $p<0.05$).

Antagonists

Specifically, the antagonists tested were: the 5-HT$_{1A}$ antagonist WAY100635 (0.1-15 mg/kg); the 5-HT$_2$ antagonist Ritanserin (10-20 mg/kg); the 5-HT$_3$ antagonist Ondansetron (1-3 mg/kg); the 5-HT$_4$ antagonist GR125487 (20-60 mg/kg); the 5-HT$_{5A}$ antagonist SB669551 (10-20 mg/kg); and the 5-HT$_7$ antagonist SB269970 (30-40 mg/kg). Studies investigating the effect of 5-HT$_6$ and 5-HT$_{1a/1b}$ antagonists are also underway.

Results: Notably, a significant ($p<0.05$) partial reversal of the FFA-induced S-IRA blockade was observed following 30-minutes treatment with the 5-HT$_4$ antagonist (GR125487, 30 mg/kg). Thus, GR125487 was effective in inducing a significant blockade of fenfluramine's inhibition of S-IRA (See FIGS. 7 and 8). Interestingly, antagonists of 5-HT$_2$, 5-HT$_4$ and 5-HT$_7$ receptors were found to reverse the anticonvulsant effect of FFA against the severity of AGSz but not its S-IRA blocking effect. The antagonists of 5-HT$_2$ (20 mg/kg Ritanserin), 5-HT$_4$ (30 and 60 mg/kg GR125487) and 5-HT$_7$ (30 mg/kg and 40 mg/kg SB269970) receptors were able to reverse FFA's anticonvulsant effect against the severity of AGSz. The 5-HT$_{5a}$ antagonist SB669551 blocked FFA's anticonvulsant effect at 20 mg/kg. In contrast, 5-HT$_{1A}$ (WAY100635 at 0.1-15 mg/kg) and 5-HT$_3$ (Ondansetron at 1-3 mg/kg) receptor antagonists were not effective at any dose tested.

Antagonists of the 5-HR$_{1A}$, 5-HT$_3$, and receptors did not reverse fenfluramine's effect, suggesting that fenfluramine's effect on S-IRA and/or AGSz is not mediated by an interaction with these receptors. In contrast, the 5-HT$_2$, 5-HT$_{5A}$, 5-HT$_7$ antagonists (Ritanserin at 20 mg/kg; SB669551 at 20 mg/kg; and SB269970 at 30 mg/kg and 40 mg/kg) were found to block FFA's anticonvulsant effect, suggesting that fenfluramine's anticonvulsant effect may be mediated by its interaction of these receptors. Notably, because the compound GR125487 was found to partially reverse fenfluramine's anticonvulsant effects and S-IRA blocking effects, it was concluded that fenfluramine was found to act specifically as an agonist at the 5-HT$_4$ receptor.

Thus, the anticonvulsant effect of FFA against S-IRA induced by AGSz in DBA/1 mice is mediated, at least in part, by activation of 5-HT$_4$ receptors. The expression level of 5-HT$_4$ receptors in the DBA/1 mouse brain is not significantly different from that in normal mice (Faingold et al., 2011). These results were surprising in light of previous studies on the receptors that mediate the ability of a selective serotonin re-uptake inhibitor to reduce seizure severity and block S-IRA can be reversed only by a selective 5-HT$_3$ antagonist (Faingold et al., 2016).

Agonists which activate specific 5-HT receptors are of interest for future studies in animal models of SUDEP and as a potential preventative treatment for human SUDEP. In some embodiments, the 5-HT agonist is a 5-HT$_4$ receptor agonist. As disclosed herein, methods of reducing incidence or severity of seizures in a human patient, comprising administering to the patient a therapeutically effective dose of a 5-HT$_4$ agonist, and allowing the 5-HT$_4$ agonist to stimulate 5-HT$_4$ receptors in the patient, can reduce the incidence and/or severity of seizures in the patient. In some embodiments, the 5-HT$_4$ agonist is fenfluramine.

Example 3

Determining the Neurotransmitter(s) that Mediate the Anticonvulsant Effect and S-IRA Blocking Effect of Fenfluramine in DBA/1 Mice Because FFA significantly and selectively elevates ambient and phasic (i.e., during postictal depression) levels of 5-HT, norepinephrine and prolactin, and because FFA is effective against AGSz and SUDEP in DBA/1 mice (as demonstrated above), studying the changes in the levels of these neurotransmitters in the central nervous system will be useful in establishing the mechanism of action of FFA. The levels of monoamines (5-HT, dopamine and norepinephrine), adenosine and prolactin vis-a-vis the levels of FFA and nor-fenfluramine will be analyzed using liquid chromatography coupled with mass spectroscopy (LC-MS) in DBA/1 mouse plasma and brains at time-points and doses of FFA found to be effective in blocking AGSz and S-IRA in DBA/1 mice.

Example 4

Potentiation of FFA's Effect on Audiogenic Seizures (AGSz) and Seizure-Induced Respiratory Arrest (S-IRA) in DBA/1 Mice by Serotonin Precursor Fenfluramine acts by augmenting 5-HT release in the central nervous system. Thus, the potentiation effect of concomitant administration of 5-hydroxytryptophan (5-HTP), the serotonin precursor, with fenfluramine will be studied as it effects the AGSz and S-IRA in DBA/1 mice. One goal of these studies, is to further reduce the dose of the drug without compromising efficacy.

Example 5

Identification of Brain Regions in DBA/1 Mice Undergoing Severe Hypoxia During S-IRA and SUDEP Seizure-induced brain dysfunction is mediated by hypoperfusion and results in severe hypoxia in discrete brain regions (Farrell et al., 2016, 2017). Thus, the brain regions that experience severe hypoxia and which may play a role in the pathogenesis of SUDEP in DBA/1 mice will be elucidated. These brain regions are the pharmacological targets for FFA. The differences in the uptake of pimonidazole hydrochloride (Hypoxyprobe™ kit) following S-IRA and its blockade with FFA will be studied, the regional colocalization of 5-HT$_4$ and Sigma 1a receptors will be established, and the brain region and receptor(s) mediating the effect of FFA against AGSz and S-IRA in DBA/1 mice will be elucidated.

Example 6

Effect of Fenfluramine on EEG, ECG and Respiration During AGSz and S-IRA in DBA/1 Mice These studies will enable determination of the physiological changes activated by FFA. The effect of the fenfluramine on the time-course of changes in EEG, EKG and respiratory activity will be determined during AGSz and S-IRA, and compared with S-IRA blockade following FFA treatment in DBA/1 mice.

Example 7

Further Studies of FFA's Anticonvulsant and S-IRA Blocking Effects

First, because the 5-HT$_4$ receptor antagonist (GR125487) was able to significantly reverse the anticonvulsant and S-IRA blocking effects of FFA in the DBA/1 mouse model, further studies will be conducted to investigate the anticonvulsant and S-IRA blocking potential of additional 5-HT$_4$ receptor agonists. For example, 10-30 mg/kg BIMU8, alone and in combination with FFA, will be assessed for its effects on AGSz and S-IRA (Manzke et al., 2003; Hasebe et al., 2015).

Additionally, the effect of 5-HT$_4$ receptor agonists (e.g., fenfluramine) on reducing ameliorating and/or eliminating seizures, and/or S-IRA and/or SUDEP in a clinical study in humans has been assessed.

Additionally, intracerebrovasular microinjection of GR125487 (10, 20 and 40 nmol) will be performed to further investigate the effects of fenfluramine or other 5-HT$_4$ receptor agonists on FFA-like targets in the brain (See De Deurwaerdere et al., 2002; Consolo et al., 1994).

Furthermore, because the 5-HT$_4$ receptor antagonist significantly reduced the anticonvulsant and S-IRA suppressant effects of FFA, the role of Sigma 1 receptors in mediating the effect will be investigated. The efficacy of a Sigma 1 receptor antagonist, NE-100, as compared to Sigma 2 antagonist (YUN252), in reversing the effect of FFA on AGSz and the incidence of S-IRA in DBA/1 mice will be studied.

Finally, if Sigma receptor antagonists are able to affect the action of FFA in DBA/1 mice, a follow-up study for the effect of Sigma 1 or 2 agonists and positive allosteric modulator, E1R (10-75 mg/kg), on AGSz and S-IRA in DBA/1 mice will be conducted to further validate this mechanism.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

I claim:

1. A method of reducing likelihood of seizure-induced Sudden Unexpected Death in Epilepsy (SUDEP) in a human patient, comprising:
    diagnosing the patient with an elevated possibility of SUDEP; and
    administering to the patient a therapeutically effective dose of a 5-HT$_4$ agonist; and
    allowing the 5-HT$_4$ agonist to stimulate 5-HT$_4$ receptors in the patient, thereby reducing the likelihood of SUDEP in the patient.

2. The method of claim 1, wherein the 5-HT$_4$ agonist is selected from the group consisting of fenfluramine, BIMU-8, Cisapride, Mosapride, Prucalopride, Renzapride, RS-67506, Tegaserod, Zacopride, Metoclopramide, and Sulpiride, or a pharmaceutically acceptable salt thereof.

3. The method of claim 1, wherein the 5-HT$_4$ agonist is fenfluramine, or a pharmaceutically acceptable salt thereof.

4. The method of claim 3, further comprising:
    diagnosing the patient as being particularly susceptible to suffering from SUDEP;
wherein fenfluramine is administered as an adjunctive therapeutic agent.

5. The method of claim 4, wherein the therapeutically effective dose of fenfluramine is selected from the group consisting of 0.2 mg/kg/day to 0.08 mg/kg/day up to a 30 mg maximum daily dose.

6. The method of claim 5, wherein the therapeutically effective dose of fenfluramine is administered in an oral liquid dosage form.

7. The method of claim 6, further comprising:
    administering to the patient an effective dose of stiripentol or a pharmaceutically acceptable salt thereof.

8. The method of claim 7, further comprising:
    administering to the patient an effective dose of valproate or a pharmaceutically acceptable salt thereof.

9. The method of claim 8, further comprising:
administering to the patient an effective dose of clobazam or a pharmaceutically acceptable salt thereof.

10. The method of claim 3, wherein fenfluramine is the only pharmaceutically active drug administered to the patient.

11. A method of reducing the length of the mean post-ictal depression (PID) period in a human patient, comprising:
diagnosing the patient with PID; and
administering to the patient a therapeutically effective dose of a $5\text{-HT}_4$ agonist; and
allowing the $5\text{-HT}_4$ agonist to stimulate $5\text{-HT}_4$ receptors in the patient, thereby inhibiting PID period in the patient.

12. The method of claim 11, wherein the $5\text{-HT}_4$ agonist is selected from the group consisting of fenfluramine, BIMU-8, Cisapride, Mosapride, Prucalopride, Renzapride, RS-67506, Tegaserod, Zacopride, Metoclopramide, and Sulpiride, or a pharmaceutically acceptable salt thereof.

13. The method of claim 11, wherein the $5\text{-HT}_4$ agonist is fenfluramine, or a pharmaceutically acceptable salt thereof.

14. The method of claim 13, further comprising:
diagnosing the patient as being particularly susceptible to suffering from PID;
wherein fenfluramine is administered as an adjunctive therapeutic agent.

15. The method of claim 14, wherein the therapeutically effective dose of fenfluramine is selected from the group consisting of 0.2 mg/kg/day to 0.08 mg/kg/day up to a 30 mg maximum daily dose.

16. The method of claim 15, wherein the therapeutically effective dose of fenfluramine is administered in an oral liquid dosage form.

17. The method of claim 16, further comprising:
administering to the patient an effective dose of stiripentol or a pharmaceutically acceptable salt thereof.

18. The method of claim 17, further comprising:
administering to the patient an effective dose of valproate or a pharmaceutically acceptable salt thereof.

19. The method of claim 18, further comprising:
administering to the patient an effective dose of clobazam or a pharmaceutically acceptable salt thereof.

20. The method of claim 13, wherein fenfluramine is the only pharmaceutically active drug administered to the patient.

21. A method of reducing likelihood of seizure-induced Sudden Unexpected Death in Epilepsy (SUDEP) in a human patient, comprising:
diagnosing the patient with an elevated possibility of SUDEP;
administering to the patient a therapeutically effective dose of fenfluramine; and
allowing the fenfluramine to stimulate $5\text{-HT}_4$ receptors in the patient, thereby reducing the likelihood of SUDEP in the patient;
wherein the therapeutically effective dose of fenfluramine consisting of 0.2 mg/kg/day to 0.08 mg/kg/day up to a 30 mg maximum daily dose.

\* \* \* \* \*